(12) United States Patent
Meyer et al.

(10) Patent No.: US 12,427,069 B2
(45) Date of Patent: Sep. 30, 2025

(54) REDUCED-LEAKAGE TAMPON

(71) Applicant: TAMPRO INC., San Francisco, CA (US)

(72) Inventors: Greta Catherine Meyer, San Francisco, CA (US); Amanda Paige Calabrese, San Francisco, CA (US); Elijah John Sampson Zenger, New York, NY (US)

(73) Assignee: TAMPRO INC., San Francisco, CA (US)

( * ) Notice: Subject to any disclaimer, the term of this patent is extended or adjusted under 35 U.S.C. 154(b) by 393 days.

(21) Appl. No.: 18/043,122

(22) PCT Filed: Aug. 30, 2021

(86) PCT No.: PCT/US2021/048256
§ 371 (c)(1),
(2) Date: Feb. 27, 2023

(87) PCT Pub. No.: WO2022/051228
PCT Pub. Date: Mar. 10, 2022

(65) Prior Publication Data
US 2024/0041664 A1   Feb. 8, 2024

Related U.S. Application Data

(60) Provisional application No. 63/073,345, filed on Sep. 1, 2020.

(51) Int. Cl.
*A61F 13/20*   (2006.01)
*A61F 13/34*   (2006.01)

(52) U.S. Cl.
CPC ...... *A61F 13/2034* (2013.01); *A61F 13/2037* (2013.01); *A61F 13/34* (2013.01)

(58) Field of Classification Search
CPC .............. A61F 13/2034; A61F 13/2031; A61F 13/202; A61F 13/2042; A61F 13/2048;
(Continued)

(56) References Cited

U.S. PATENT DOCUMENTS 3,818,912 A   6/1974   Etz
4,328,804 A   5/1982   Shimatani
(Continued)

FOREIGN PATENT DOCUMENTS

AU   2012257503   1/2016
CN   103705346   11/2018
(Continued)

OTHER PUBLICATIONS

O.b. Applicator Free Digital Tampons, first available Dec. 29, 2010, amazon.com, [online], [site visited Feb. 23, 2022], Available w from internet URL: https://www.amazon.com/b-Applicator-Digital-Super-Plus/dp/BOONJ NJCBI/ref=sr_1_ 121 ?crid=1341688HYH LDM &keywords=tampon&qid=164562670%E2%80%A6 (Year: 2010).

(Continued)

*Primary Examiner* — Susan S Su
(74) *Attorney, Agent, or Firm* — Knobbe, Martens, Olson & Bear, LLP

(57) ABSTRACT

Tampons including an elongate body and a removal string extending from a removal end of the elongate body. The tampons may include a flow path that directs menses across the elongate body. The tampons may include a plurality of longitudinal ribs crossing the flow path. The plurality of longitudinal ribs facilitate expansion of the elongate body.

21 Claims, 15 Drawing Sheets

(58) Field of Classification Search
CPC .... A61F 13/2045; A61F 13/2051–2074; A61F 13/2077–208
See application file for complete search history.

(56) References Cited

U.S. PATENT DOCUMENTS

| | | | |
|---|---|---|---|
| 4,335,720 A | 6/1982 | Glassman | |
| 4,335,721 A | 6/1982 | Matthews | |
| 4,412,833 A | 11/1983 | Wiegner et al. | |
| 4,453,925 A | 6/1984 | Decker | |
| 5,047,024 A | 9/1991 | Glassman | |
| 5,084,038 A | 1/1992 | Sheldon et al. | |
| 5,153,971 A | 10/1992 | Iten | |
| 5,185,010 A | 2/1993 | Brown, Jr. | |
| 5,201,326 A | 4/1993 | Kubicki et al. | |
| D354,561 S | 1/1995 | Tostrup | |
| 5,403,300 A | 4/1995 | Howarth | |
| 5,592,725 A | 1/1997 | Brinker | |
| 5,659,934 A | 8/1997 | Jessup et al. | |
| 5,807,372 A | 9/1998 | Balzar | |
| 5,813,102 A | 9/1998 | Leutwyler et al. | |
| D401,385 S | 11/1998 | Mintz | |
| 5,832,576 A | 11/1998 | Leutwyler et al. | |
| D401,735 S | 12/1998 | Rom | |
| 5,873,971 A | 2/1999 | Balzar | |
| 5,891,081 A | 4/1999 | McNellis et al. | |
| 5,891,123 A | 4/1999 | Balzar | |
| 5,909,884 A | 6/1999 | Schwankhart | |
| 5,911,712 A | 6/1999 | Leutwyler et al. | |
| D415,565 S | 10/1999 | Hayes et al. | |
| 6,039,716 A | 3/2000 | Jessup et al. | |
| 6,152,905 A | 11/2000 | Osborn, III et al. | |
| 6,177,608 B1 | 1/2001 | Weinstrauch | |
| 6,186,995 B1 | 2/2001 | Tharpe, Jr. | |
| 6,310,269 B1 | 10/2001 | Friese et al. | |
| 6,433,246 B1 | 8/2002 | Nguyen et al. | |
| D477,075 S | 7/2003 | Schoelling | |
| D485,354 S | 1/2004 | Carlin et al. | |
| D492,033 S | 6/2004 | Jarmon et al. | |
| 6,743,212 B1 | 6/2004 | Cole et al. | |
| 6,748,634 B2 | 6/2004 | Nguyen et al. | |
| 6,874,394 B1 | 4/2005 | Hull, Jr. et al. | |
| 6,889,409 B2 | 5/2005 | Friese et al. | |
| 6,939,340 B1 | 9/2005 | Berges | |
| 6,953,456 B2 | 10/2005 | Fuchs et al. | |
| D511,572 S | 11/2005 | Weber et al. | |
| D511,829 S | 11/2005 | Phipps et al. | |
| D511,830 S | 11/2005 | Turchi et al. | |
| D511,831 S | 11/2005 | Turchi et al. | |
| D511,832 S | 11/2005 | Bellofatto et al. | |
| D512,142 S | 11/2005 | Weber et al. | |
| D512,143 S | 11/2005 | Weber et al. | |
| D512,144 S | 11/2005 | Weber et al. | |
| D512,145 S | 11/2005 | Turchi et al. | |
| D512,146 S | 11/2005 | Phipps et al. | |
| D513,321 S | 12/2005 | Turchi et al. | |
| D514,700 S | 2/2006 | Weber et al. | |
| D515,212 S | 2/2006 | Edgett et al. | |
| D517,210 S | 3/2006 | Weber et al. | |
| D517,691 S | 3/2006 | Turchi et al. | |
| D517,692 S | 3/2006 | Weber et al. | |
| 7,059,026 B2 | 6/2006 | Friese et al. | |
| 7,060,057 B2 | 6/2006 | Policappelli | |
| 7,070,585 B2 | 7/2006 | Jensen | |
| D559,983 S | 1/2008 | Edgett et al. | |
| D568,472 S | 5/2008 | Sargent, Jr. et al. | |
| D568,995 S | 5/2008 | Sargent, Jr. et al. | |
| D572,362 S | 7/2008 | Edgett et al. | |
| D602,153 S | 10/2009 | Osterberg | |
| D615,202 S | 5/2010 | Edgett et al. | |
| 7,713,253 B2 | 5/2010 | Osborn, III et al. | |
| D620,592 S | 7/2010 | VanDenBogart et al. | |
| 7,833,210 B2 | 11/2010 | Schoelling | |
| D631,153 S | 1/2011 | McGlothlin et al. | |
| 7,977,532 B2 | 7/2011 | Hasse et al. | |
| 7,994,387 B2 | 8/2011 | Minoguchi et al. | |
| D647,610 S | 10/2011 | Smet | |
| D647,611 S | 10/2011 | Smet | |
| D647,612 S | 10/2011 | Smet | |
| 8,029,485 B2 | 10/2011 | Jensen | |
| 8,048,053 B2 | 11/2011 | Minoguchi et al. | |
| 8,082,639 B2 | 12/2011 | Rolli | |
| D655,058 S | 2/2012 | Blair | |
| D662,168 S | 6/2012 | Sims et al. | |
| D662,590 S | 6/2012 | Sanoi et al. | |
| 8,221,371 B2 | 7/2012 | Junio et al. | |
| 8,353,890 B2 | 1/2013 | Schoelling | |
| 8,403,879 B2 | 3/2013 | Schoelling | |
| 8,460,262 B2 | 6/2013 | Fung et al. | |
| 8,468,662 B2 | 6/2013 | Rolli et al. | |
| 8,474,114 B2 | 7/2013 | Rolli | |
| 8,475,425 B2 | 7/2013 | Hasse et al. | |
| D690,806 S | 10/2013 | Nakayama et al. | |
| 8,568,381 B2 | 10/2013 | Mueller et al. | |
| 8,574,210 B2 | 11/2013 | Ingelgem et al. | |
| D697,610 S | 1/2014 | Young | |
| D698,451 S | 1/2014 | Tai | |
| D701,600 S | 3/2014 | Kauffman | |
| 8,702,670 B2 | 4/2014 | Biggs et al. | |
| 8,735,647 B2 | 5/2014 | Schoelling | |
| 8,747,378 B2 | 6/2014 | Van Ingelgem et al. | |
| D709,610 S | 7/2014 | Pick | |
| 8,771,248 B2 | 7/2014 | Watanabe et al. | |
| 8,777,916 B2 | 7/2014 | Ingelgem et al. | |
| D713,029 S | 9/2014 | Shiraishi et al. | |
| 8,827,974 B2 | 9/2014 | Schmidt-Forst | |
| 8,827,975 B2 | 9/2014 | Kimball et al. | |
| 8,834,438 B2 | 9/2014 | Kinoshita et al. | |
| 8,834,439 B2 | 9/2014 | Kimball et al. | |
| 8,864,732 B2 | 10/2014 | Van Ingelgem et al. | |
| D717,430 S | 11/2014 | Shiraishi et al. | |
| D717,950 S | 11/2014 | Agrawal | |
| 8,882,734 B2 | 11/2014 | Drevik | |
| D719,653 S | 12/2014 | Agrawal | |
| 8,905,989 B2 | 12/2014 | Fung et al. | |
| 8,916,015 B2 | 12/2014 | McDaniel et al. | |
| D721,218 S | 1/2015 | Rogers et al. | |
| 8,938,866 B2 | 1/2015 | Amundson et al. | |
| 9,050,215 B2 | 6/2015 | Zabret | |
| 9,078,787 B2 | 7/2015 | Gehling et al. | |
| 9,125,771 B2 | 9/2015 | Schoelling | |
| 9,138,355 B2 | 9/2015 | Hasse et al. | |
| D741,479 S | 10/2015 | Agrawal | |
| D741,480 S | 10/2015 | Chavan et al. | |
| 9,155,666 B2 | 10/2015 | Smet et al. | |
| 9,168,184 B2 | 10/2015 | Kimball et al. | |
| 9,173,778 B2 | 11/2015 | Schoelling | |
| 9,205,004 B2 | 12/2015 | Watanabe et al. | |
| 9,211,216 B2 | 12/2015 | McDaniel et al. | |
| 9,211,217 B2 | 12/2015 | Tomosovic et al. | |
| 9,308,134 B2 | 4/2016 | Wolter et al. | |
| 9,610,201 B2 | 4/2017 | Schmidt-Forst et al. | |
| D789,651 S | 6/2017 | Wilson et al. | |
| D793,650 S | 8/2017 | Herrenbruck | |
| D804,655 S | 12/2017 | Holliday et al. | |
| 9,849,041 B2 | 12/2017 | Wolter et al. | |
| 9,861,535 B2 | 1/2018 | Mueller | |
| 9,877,877 B2 | 1/2018 | Edgett et al. | |
| D816,839 S | 5/2018 | Buell et al. | |
| D817,894 S | 5/2018 | Ganske | |
| D818,130 S | 5/2018 | Jacobson | |
| D819,206 S | 5/2018 | Buell | |
| D819,813 S | 6/2018 | Buell et al. | |
| 10,010,456 B2 | 7/2018 | Kimball et al. | |
| 10,010,457 B2 | 7/2018 | Kimball et al. | |
| D827,849 S | 9/2018 | Marshall | |
| 10,076,452 B2 | 9/2018 | Jorgensen et al. | |
| 10,098,793 B2 | 10/2018 | Schoelling | |
| D834,189 S | 11/2018 | Cohen et al. | |
| D839,737 S | 2/2019 | Pinard | |
| D842,492 S | 3/2019 | Lurchenko | |
| D842,993 S | 3/2019 | Buell et al. | |
| D844,281 S | 4/2019 | Erol | |
| 10,245,189 B2 | 4/2019 | Schoelling | |

(56) References Cited

U.S. PATENT DOCUMENTS

| | | |
|---|---|---|
| 10,342,712 B1 | 7/2019 | McCrory |
| D861,186 S | 9/2019 | Matsuura et al. |
| D861,909 S | 10/2019 | Cheung |
| D868,989 S | 12/2019 | Marshall |
| D872,861 S | 1/2020 | Adams |
| D876,047 S | 2/2020 | Herrenbruck |
| 10,596,046 B2 | 3/2020 | Jorgensen et al. |
| D882,766 S | 4/2020 | Baik et al. |
| D884,881 S | 5/2020 | Kimball |
| 10,667,959 B2 | 6/2020 | Gehling et al. |
| D890,922 S | 7/2020 | Baik et al. |
| D927,686 S | 8/2021 | Calabrese et al. |
| 11,154,430 B2 | 10/2021 | Edgett et al. |
| 11,285,052 B2 | 3/2022 | Cohen et al. |
| 11,395,770 B2 | 7/2022 | Kimball |
| D977,632 S | 2/2023 | Meyer et al. |
| 2002/0022816 A1 | 2/2002 | Knox |
| 2002/0151859 A1 | 10/2002 | Schoelling |
| 2003/0093049 A1 | 5/2003 | Johnson |
| 2003/0097104 A1 | 5/2003 | Gilbert |
| 2003/0149416 A1 | 8/2003 | Cole et al. |
| 2003/0208179 A1 | 11/2003 | Fuchs et al. |
| 2003/0233813 A1 | 12/2003 | Leslie et al. |
| 2005/0096619 A1 | 5/2005 | Costa |
| 2005/0096620 A1 | 5/2005 | Awolin et al. |
| 2005/0113787 A1 | 5/2005 | Carlin |
| 2006/0025742 A1 | 2/2006 | Hasse et al. |
| 2006/0025743 A1 | 2/2006 | Hasse et al. |
| 2006/0185136 A1 | 8/2006 | Friese et al. |
| 2007/0073257 A1 | 3/2007 | Buck et al. |
| 2008/0077106 A1 | 3/2008 | Minoguchi et al. |
| 2008/0154222 A1 | 6/2008 | Chaffringeon |
| 2008/0200892 A1 | 8/2008 | Ingelgem et al. |
| 2008/0200895 A1 | 8/2008 | Minoguchi et al. |
| 2008/0221502 A1 | 9/2008 | Binner et al. |
| 2010/0152642 A1 | 6/2010 | Kim et al. |
| 2011/0092940 A1 | 4/2011 | Fung et al. |
| 2011/0215025 A1 | 9/2011 | Gonzalez |
| 2011/0238028 A1 | 9/2011 | Smet |
| 2012/0010587 A1 | 1/2012 | Smet |
| 2012/0089111 A1 | 4/2012 | Magnusson |
| 2012/0165599 A1 | 6/2012 | Ellefson et al. |
| 2012/0187600 A1 | 7/2012 | Graber |
| 2013/0160259 A1* | 6/2013 | McDaniel ............ A61F 13/2022 28/120 |
| 2014/0066871 A1 | 3/2014 | Shepard et al. |
| 2014/0188064 A1 | 7/2014 | Yamaki |
| 2016/0235583 A1 | 8/2016 | Durling et al. |
| 2018/0207036 A1 | 7/2018 | Chien |
| 2018/0333308 A1 | 11/2018 | Zhu |
| 2019/0099303 A1 | 4/2019 | Viens et al. |
| 2019/0216655 A1 | 7/2019 | Gehling et al. |
| 2019/0269561 A1 | 9/2019 | Cohen et al. |
| 2019/0314213 A1 | 10/2019 | Graham |
| 2020/0163806 A1 | 5/2020 | Jorgensen et al. |
| 2020/0306098 A1 | 10/2020 | Lin |
| 2021/0007904 A1 | 1/2021 | Kimbal |
| 2021/0093486 A1 | 4/2021 | Buschhaus et al. |
| 2021/0093487 A1 | 4/2021 | Brooks et al. |
| 2021/0220184 A1 | 7/2021 | Milanova |
| 2022/0047428 A1 | 2/2022 | Helvits et al. |
| 2022/0051228 A1 | 2/2022 | Guo et al. |
| 2022/0133549 A1 | 5/2022 | Meyer et al. |
| 2022/0211555 A1 | 7/2022 | Buschhaus et al. |
| 2023/0051364 A1 | 2/2023 | Vendrell Vila |

FOREIGN PATENT DOCUMENTS

| | | |
|---|---|---|
| EP | 685213 | 10/2001 |
| EP | 1022004 | 12/2003 |
| EP | 1481656 | 1/2004 |
| EP | 1244402 | 7/2006 |
| EP | 1683503 | 7/2006 |
| EP | 1383453 | 8/2006 |
| EP | 1765242 | 3/2007 |
| EP | 2184044 | 5/2010 |
| EP | 1304094 | 3/2011 |
| EP | 1304095 | 3/2011 |
| EP | 2311419 | 4/2011 |
| EP | 2285329 | 5/2013 |
| EP | 2417954 | 7/2013 |
| EP | 1759678 | 3/2014 |
| EP | 2629726 | 10/2015 |
| EP | 3156022 | 4/2017 |
| EP | 2740448 | 10/2017 |
| EP | 3181105 | 6/2018 |
| JP | 2004089576 | 3/2004 |
| WO | WO 2000/053141 | 9/2000 |
| WO | WO 2001/047458 | 7/2001 |
| WO | WO 2005/077312 | 8/2005 |
| WO | WO 2008/148396 | 12/2008 |
| WO | WO 2012/053986 | 4/2012 |
| WO | WO 2018/202382 | 11/2018 |
| WO | WO 2020/180571 | 9/2020 |
| WO | WO 2020/253971 | 12/2020 |
| WO | WO 2021/029829 | 2/2021 |
| WO | WO 2021/250436 | 12/2021 |
| WO | WO 2022/081096 | 4/2022 |

OTHER PUBLICATIONS

Sequel, trysequel.com/, [online], [site visited Feb. 23, 2022], Available from internet URL: https://www.trysequel.com/ (Year: 2022).

Tempo Tampon, dated Nov. 25, 2019. Available from Internet. URL:https://cheddar.com/media/tempo-creates-new-product-to-address-the-tampon-leakage-issue. Year: 2019.

Veeda 100% Natural Cotton Applicator Free Tampons, first available Jan. 6, 2014, amazon.com, [online], [site visited feb. 23 V 2022], Available from internet URL: https://www.amazon.comNeeda-Hypoallergenic-Biodegradable-Unscented-Applicator/dp/B00HNMIPDW/ref=sr_1_131?crid=1341688HYHLDM&keyw%E2%80%A6 (Year: 2014).

International Search Report and Written Opinion in PCT Application No. PCT/US2021/048256, dated Feb. 1, 2022.

* cited by examiner

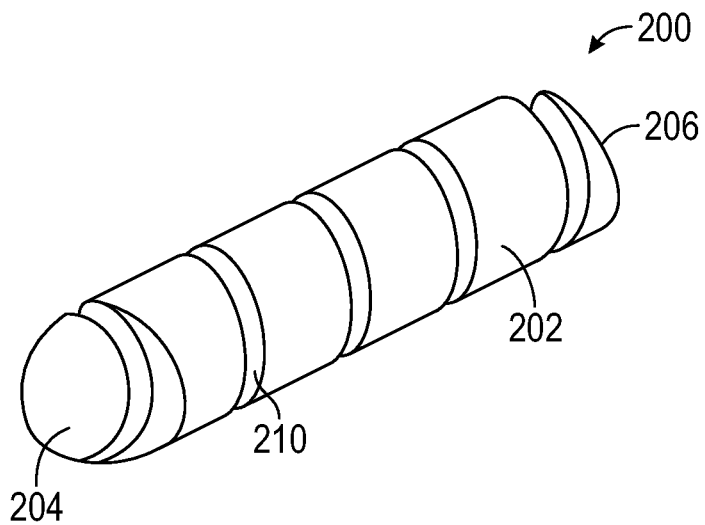
FIG. 6A
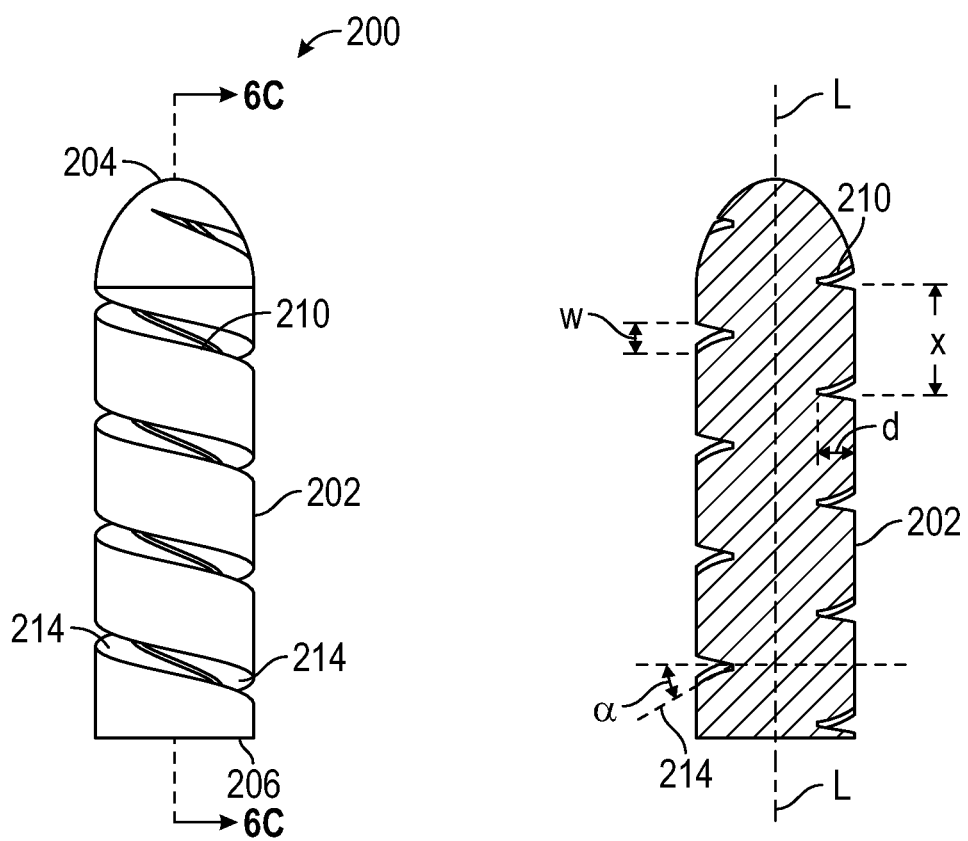
FIG. 6B  FIG. 6C

REDUCED-LEAKAGE TAMPON

BACKGROUND

Field

The present disclosure relates to tampons for feminine hygiene.

Description of the Related Art

Tampons are most commonly used to retain menstrual fluid and tissue. The fluid and tissue is absorbed and held by the tampon for a certain amount of time. After this period, the tampon is removed and a new tampon is used if the user desires.

SUMMARY

Tampons are often made of compressed absorbent fibers with a cover layer. Existing tampons include longitudinal grooving or channeling on the outside of tampons to direct a flow of menses (see FIG. 1). Within the space, however, there is still a large problem with tampons leaking before reaching significant levels of saturation and not performing as well as necessary. As a result, women have to constantly think about their tampons. This can be particularly stressful in a public setting, for example at the workplace or on the athletic field.

Tampons with the absorbent materials and flow paths described herein produce a more efficiently and evenly absorbing tampon. In several embodiments, the absorbent material absorbs the less viscous menstrual material, while the flow path redirects the more viscous menstrual material as it travels down the elongate body of the tampon in order to give it more time to absorb.

In several embodiments, the tampons described herein have one or more of the following advantages:
- slow the total travel time for menstrual material across the tampon giving the tampon more time to absorb the menstrual material;
- reduce the likelihood of possible leakage before full saturation of the tampon;
- require less frequent replacement of tampons and lower the total cost of goods required per period cycle;
- conform to the rugae along the vaginal walls to prevent displacement during active movement;
- sustainable materials, and/or
- absorb clots and more viscous material.

In some embodiments, a tampon is provided that comprises or consists essentially of a body comprising an insertion end and a removal end opposite the insertion end, a longitudinal axis of the elongate body extending through the removal end and the insertion end. In one embodiment, a plurality of longitudinal ribs protrude from an outer surface of the elongate body. A flow path may be recessed in an outer surface of the elongate body, the flow path turning about the longitudinal axis of the body, the flow path being angled closer to horizontal than the longitudinal axis of the body. A removal string or other removal device is optionally included and may include additional absorbency capability. The plurality of longitudinal ribs may converge at the insertion end to form an insertion end of the tampon. The elongate body may include an outer layer surrounding a core material. The core material may be exposed at the insertion end of the elongate body, but in other configurations, the outer layer may cover the insertion end of the elongate body. The convergence of the plurality of longitudinal ribs may guide fluid towards the internal core material. Each longitudinal rib may protrude from the outer surface of the elongate by at least about 0.5 mm and/or less than or equal to about 5 mm, for example between 1-3 mm, between 2-4 mm, between 3-5 mm, or numerical values within those ranges. A width of each rib, in a circumferential direction, may be less than or equal to about 5 mm, for example, between 3-5 mm, between 1-3 mm, between 0.5-2 mm, or numerical values within those ranges.

In some configurations, the tampon may include a body (e.g., an elongate body) having an absorbent material and one or more flow paths that direct bodily fluid (e.g., menses) across the body. In some configurations, the flow path may be a single, continuous flow path. The body may include an insertion end and a removal end opposite the insertion end. A longitudinal axis of the body extends through the removal end and the insertion end. Optionally, the tampon may also include a removal thread or string extending from the removal end of the body. Each flow path may include a fully enclosed ring (e.g., an annular ring, waved ring, zig-zag ring, etc.) or a spiral with at least one complete turn around the longitudinal axis of the body. In either configuration, the flow path may be disposed within a single plane or extend along at least a partial length of the body. In either configuration, the flow path may extend along an outer surface of the body and/or internal of the body. In configurations having a spiral flow path, the spiral flow path may have a first free end at or near the insertion end of the body (e.g., within 5% or 10% of a length of the body from the insertion end) and a second free end at or near the removal end of the body (e.g., within 5% or 10% of a length of the body from the removal end). In configurations with a spiral flow path, successive turns of a spiral flow path may have a constant or different radius. The flow path may be molded, cut, compressed, or otherwise formed into the external surface of the body, or formed by a thread wrapped around or within the body. In some implementations, the body may include an absorbent material such as bamboo.

In one embodiment, the removal string is hypoallergenic and is designed to prevent or reduce irritation to surrounding tissue. The removal string is optional and may not be included in some embodiments. The string may be looped, compressed, or elongated, and may be designed for concealment, which may be particularly beneficial for certain athletic events (such as swimming). In some embodiments, the string is absorbent and is designed to absorb a portion of the menstrual flow. In some embodiments, the string is hydrophobic and/or is designed to be waterproof or non-absorbent. In other embodiments, the string is partially absorbent and partially non-absorbent and/or has variable regions of absorbency (e.g., along the string length).

In some embodiments, the tampon may include a body (e.g., an elongate body) one or more spiral recesses in an outer surface of the body. The body may include an insertion end and a removal end opposite the insertion end. A longitudinal axis of the body extends through the removal end and the insertion end. In some configurations, the insertion end of the body may be rounded or tapered such that the insertion end has a reduced diameter compared to the removal end. Optionally, the tampon may also include a removal thread or string extending from a removal end of the body, which may extend along a partial or entire length of the body. Each spiral recess may turn about the longitudinal axis of the body. For example, each spiral recess extends at least one complete turn around a circumference of the body. Each turn of the spiral recess may be angled closer to horizontal than the longitudinal axis of the body such that each turn of the spiral recess has a greater latitudinal component than longitudinal component. For example, each turn of the spiral recess may be angled between 45 degrees and 90 degrees (e.g., between 50 degrees and 80 degrees or between 65 degrees and 75 degrees) from the longitudinal axis. With the spiral turning about the longitudinal axis, the pitch of the spiral recess may be measured in the longitudinal direction. The pitch of each spiral recess may be between 5 mm and 15 mm or between 7.5 mm and 12.5 mm. The radius of curvature of each spiral recess may be less than or equal to 8 mm or less than or equal to 6 mm. An inner surface of each spiral recess may have a tapered or rounded profile. In some configurations, the spiral recess may be tapered in a radial direction such that an opening of the spiral recess at the outer surface of the body is wider than an apex of the spiral recess. In other configurations, the opening of the spiral recess may be narrower than an opposite side of the recess (e.g., the radially inward-most edge of the recess), for example with diverging internal surfaces or a rounded profile. In some configurations, the spiral recess may be concave in a radial direction. The body may include a rounded or sharp corner between the inner surface of the spiral recess and the outer surface of the body. Each spiral recess may be formed using a mold (e.g., compression mold), a thread, compressed, cut, or otherwise formed. In some configurations, the tampon may include a single, continuous spiral recess. The spiral recess may have a first free end at or near the insertion end of the body (e.g., within 5% or within 10% of a length from the insertion end) and a second free end at or near the removal end of the body (e.g., within 5% or within 10% of a length from the removal end). Optionally, the tampon may include a plurality of longitudinal recesses in the outer surface of the body. The plurality of longitudinal recesses may cross successive turns of the spiral recess. In some implementations, the body may include an absorbent material such as bamboo.

In some embodiments, the tampon may include a body (e.g., an elongate body) having one or more spirally wrapped threads that direct a flow of bodily fluid (e.g., menses) across the body. The body may include an insertion end and a removal end opposite the insertion end. A longitudinal axis of the body extends through the removal end and the insertion end. In some configurations, the insertion end of the body may be rounded or tapered such that the insertion end has a reduced diameter compared to the removal end. Optionally, the tampon may also include a removal thread or string extending from a removal end of the body, which may extend along at least a partial or entire length of the body. Each spirally wrapped thread includes at least one complete turn around a longitudinal axis of the body. Each spirally wrapped thread may extend along an outer surface of the body to form a recess in the outer surface of the body and/or extend internally within the body. Each spirally wrapped thread may be disposed within a single plane or spiral along at least a partial length of the body. For example, in some embodiments, each thread may be spirally wrapped within a single plane. In other embodiments, each thread may be spirally wrapped such that successive turns are longitudinally displaced from each other along a length of the body. In either configuration, successive turns of the spirally wrapped thread may have a constant or varying radius. For example, in some embodiments, each spirally wrapped thread may include a first radius of curvature and a second radius of curvature that is smaller than the first radius of curvature. In some configurations, the second radius of curvature may be closer to the removal end, but in other configurations, the first radius of curvature may be closer to the removal end. In some implementations, the body may include an absorbent material such as bamboo.

In some embodiments, the tampon may include a body, for example an elongate body having an insertion end and a removal end. A removal string may extend from the removal end of the elongate body. The tampon may include one or more ribs protruding from an outer surface of the elongate body. The one or more ribs may extend in a generally longitudinal direction. The one or more ribs may extend across at least a majority of a length of the elongate body or substantially the entire length of the elongate body. The one or more ribs may be integral with or joined to the elongate body. The one or more ribs may include a constant or varied thickness. The one or more ribs may be spaced apart from the insertion end of the elongate body or converge to form an insertion tip of the tampon. Each rib includes an outer edge. Portions of the outer edge may be recessed compared to adjacent portions of the outer edge. For example, portions of the rib crossing the flow path may be recessed compared to portions of the outer edge away from the flow path. Alternatively, the outer edge of each rib may be generally straight or smooth without any recessed portions. Optionally, the tampon may include any one or combination of flow paths described herein. For example, the tampon may include a flow path recessed in an outer surface of the elongate body. The flow path may direct a flow of menses about the longitudinal axis of the body, for example in a spiral path around the elongate body. The flow path may include a continuous spiral recess interrupted by the plurality of longitudinal ribs, or a plurality of recessed segments disposed between adjacent longitudinal ribs. The turns of the flow path may be angled closer to horizontal than the longitudinal axis of the body, for example at an angle between 50 degrees and 80 degrees from the longitudinal axis of the body. Each turn of the flow path may extend at the same angle relative to the longitudinal axis of the body. Strings or other removal devices as described in other embodiments may be included. Such strings or other removal devices may include additional absorbency or elements to reduce leakage. Alternatively, the string or other removal device may not be included or may be nonabsorbent.

In some embodiments, methods of manufacturing a tampon include forming a body (e.g., an elongate body) of the tampon from an absorbent material. For example, a layer of the absorbent material may be formed into the body. The method may include rolling the layer of absorbent material to form the body. In some configurations, the layer of absorbent material may have parallel fibers. When the body is formed, the fibers may be oriented in a direction perpendicular to the longitudinal axis of the body. Optionally, a retrieval thread or string may be attached to the layer of absorbent material. A spiral flow path may be formed in an outer surface of the body such that the spiral flow path turns about a longitudinal axis of the body. In some methods, the spiral flow path may be formed by compressing the outer surface, for example by using a mold (e.g., a compression mold). In some methods, longitudinal ribs may be formed between segments of the mold. The mold may cinch or compress the insertion end of the elongate body to form an insertion tip of the tampon. In some methods, the spiral flow path may be formed by applying a thread around the outer surface of the body. In some methods, the spiral flow path may be cut or otherwise formed in the body. In this method, the thread may be bonded or otherwise attached to the outer surface of the body.

Certain aspects of the disclosure relate to a tampon having an elongate body with an insertion end, a removal end opposite the insertion end, and a longitudinal axis extending through the removal end and the insertion end. The tampon may include one or more flow paths recessed in an outer surface of the elongate body. The one or more flow paths may take on a generally spiral configuration. For example, the flow path may form a single spiral turning about the longitudinal axis of the elongate body. The flow path may include a single entry point near the insertion end and a single termination point near the removal end. In addition or alternative to the flow path, the tampon may include a plurality of ribs protruding from an outer surface of the elongate body. The ribs may begin at or adjacent an insertion end of the elongate body and terminate at or adjacent a removal end of the elongate body. Each of the plurality of ribs may extend in a longitudinal direction. The plurality of ribs may be generally straight and/or aligned with the longitudinal axis of the elongate body, but in other configurations, may be angled, curved, waved, or shaped otherwise relative to the longitudinal axis. Each rib may intersect the flow path at one or more axially locations but still permit flow along the flow path. The plurality of ribs may converge at or toward the insertion end of the elongate body. The insertion end may have a reduced diameter compared to a remainder of the elongate body.

The elongate body may include an absorbent core surrounded by an overwrap layer. The overwrap layer may be sealed at the insertion end and open at the removal end to expose the absorbent core. In some embodiments, the plurality of ribs may be formed only by the overwrap layer.

Certain aspects of the disclosure relate to a tampon having an elongate body with an insertion end, a removal end opposite the insertion end, and a longitudinal axis extending through the removal end and the insertion end. The tampon may include a plurality of discrete flow path segments recessed in an outer surface of the elongate body. Each flow path segment may be angled closer to horizontal than the longitudinal axis. The flow path segments may be spaced apart from each other in the circumferential and/or longitudinal direction. Combined, the plurality of flow path segments may take on a generally spiral configuration turning about the longitudinal axis of the elongate body. The tampon may include a plurality of longitudinal ribs protruding from an outer surface of the elongate body, for example at least six ribs or at least eight ribs. The plurality of longitudinal ribs separate the plurality of flow segments. For example, circumferentially adjacent flow segments may be separated by one of the longitudinal ribs. The longitudinal ribs may begin at or adjacent an insertion end of the elongate body and terminate at or adjacent a removal end of the elongate body. Each longitudinal rib may have a substantially constant width along its length. The plurality of longitudinal ribs may converge at or toward the insertion end of the elongate body. The insertion end may have a reduced diameter compared to a remainder of the elongate body. Upon saturation of the tampon, the outer surface of the elongate body may expand relative to outer edges of the plurality of longitudinal ribs to reduce a thickness of the plurality of longitudinal ribs.

Certain aspects of the disclosure are directed toward a method of manufacturing a tampon. The method may include forming an absorbent core. The absorbent core may be formed by rolling a layer of absorbent material. The method may include attaching a retrieval string to the absorbent core, for example by looping the retrieval string around the layer of absorbent material. The retrieval string may be attached prior to rolling the layer of absorbent material. The method may include applying an overwrap layer to the absorbent core to form an elongate body. The overwrap layer may be applied by inserting the absorbent core into a tubular overwrap layer. One end of the tubular overwrap layer may be sealed prior to inserting the absorbent core into the tubular overwrap layer. The method may include compressing the elongate body to form one or more recessed flow paths in an outer surface of the elongate body. The one or more recessed flow paths may form a generally spiral flow path. The method may also include extruding a plurality of longitudinal ribs that intersect the one or more flow paths. The compression and extrusion steps may occur simultaneously using a compression mold. For example, the one or more recessed flow paths may be formed by mold segments of the compression mold, while the ribs are extruded between the mold segments. The method may also include cinching an insertion end of the elongate body using the plurality of mold segments.

Any of the tampons described herein may be incorporated into a kit. In some embodiments, a kit may include a plurality of tampons. Each of the plurality of tampons may include a body (e.g., an elongate body) having an insertion end and a removal end opposite the insertion end. A longitudinal axis of the body extends through the insertion end and the removal end. Each of the plurality of tampons may include a flow path configured to direct menses across the body. The flow path may provide at least one complete turn about the longitudinal axis of the body. Each tampon may include a same type or different types of flow paths as described herein. Optionally, each of the plurality of tampons may include a removal thread or string extending from a removal end of the body. In some kits, the plurality of tampons includes at least two different sized tampons providing different levels of absorbency. The kit may include one or more menstrual pads, period underwear, and/or panty liners.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIGS. 6A-6C illustrate a tampon having a spiral flow path.

DETAILED DESCRIPTION

With the absorbent materials and/or flow paths outlined herein, tampons, according to some embodiments, exhibit higher comfort, performance, and sustainability. The tampons described herein, in one embodiment, reduce the likelihood of premature leakage before the absorbent material is fully saturated. The tampons according to several embodiments described herein are particularly advantageous because they offer reduced leakage before full saturation of the tampon to active women, including athletes, who do not have the ability to leave and check their tampon. This allows women to stay engaged and focused without worrying about leakage.

Figure 1:
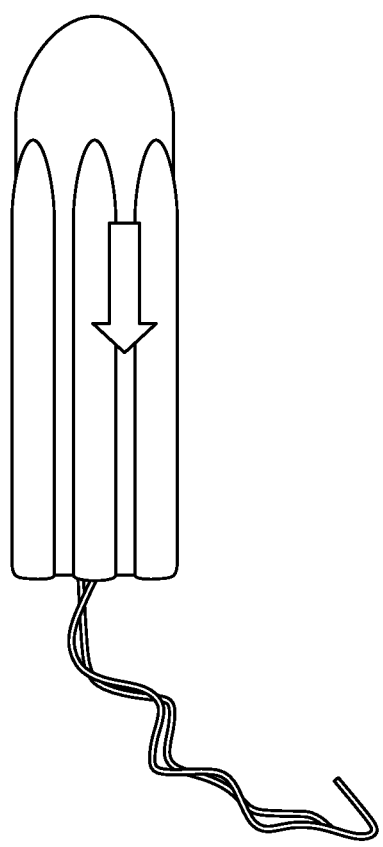
FIG. 1 illustrates a tampon with a longitudinal flow path to direct a flow of menses.
Figure 2:
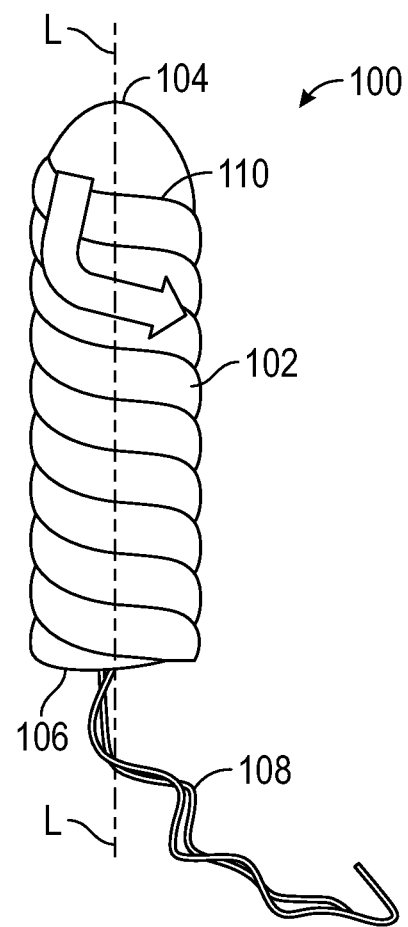
FIG. 2 illustrates a tampon with spiral flow path to direct a flow of menses.

FIG. 2 illustrates a tampon 100 having a body 102 with a first or insertion end 104 and a second or removal end 106. The body 102 may have an elongate shape, for example a generally cylindrical shape. The first end 104 of the elongate body 102 may be rounded and/or tapered to facilitate insertion of the tampon 100. The end face of the first end 104 may have a rounded or flat profile. The first end 104 of the elongate body 102 may have a reduced diameter compared to the second end 106 of the elongate body 102. The second end 106 of the elongate body 102 may include a flattened base. As illustrated, the elongate body 102 has a rounded cone portion and a cylindrical base portion, but in other configurations, the elongate body 102 may be entirely cylindrical.

The length of the elongate body 102, measured along a longitudinal axis L of the elongate body 102, may be greater than a width of the elongate body 102, measured along an axis perpendicular to the longitudinal axis L. For example, the length of the elongate body 102 may be at least three times or at least four times greater than the width of the elongate body 102. The length of the elongate body 102 can be less than or equal to about 7 cm, less than or equal to about 6 cm, or less than or equal to about 5 cm, for example between about 4 cm and about 6 cm. A width of the second end 106 of the elongate body 102 can be less than or equal to about 1.5 cm (e.g., 1.25-1.5 cm, 1.0-1.25 cm, 0.75-1.0 cm and numerical values in between), while a width of the first end 104 of the elongate body 104 can be less than or equal to about 1.0 cm (e.g., 0.75-1.0 cm, 0.5-0.75 cm, 0.25-0.5 cm and numerical values in between). A total mass of the elongate body 102 can be between about 1.5 g and about 2.5 g, for example between about 1.9 g and about 2.1 g.

The tampon 100 may also include a removal string 108 extending from the second end 106 of the elongate body 102. The removal string 108 facilitates removal of the elongate body 102 without tearing or breaking the tampon 100. The removal string 108 may extend through at least a portion of the elongate body 102. For example, as explained below with respect to FIG. 8A, the removal string 108 may extend along the entire length or substantially the entire length of the elongate body 102. The removal string 108 may be a single fiber or include a plurality of fibers braided together. The removal string 108 may include cotton, polyester, polypropylene, rayon, or a blended material including any of the aforementioned materials.

The elongate body 102 includes at least one flow path 110 configured to direct a flow of menses across the elongate body 102. The flow path 110 may at least partially direct a flow of menses in a latitudinal direction. The flow path 110 may be visually distinct from adjacent portions of the elongate body 102. As shown in FIG. 2, the elongate body 102 includes a single, continuous flow path 110 that directs a flow of menses along an external surface of the elongate body 102. However, as described in more detail below, the flow path 110 may direct a flow of menses internally through the elongate body 102 in addition to, or in alternative to, directing flow along the external surface of the elongate body 102. The flow path 110 extends at least one complete turn around a circumference or perimeter of the elongate body 102 or within the elongate body 102. The complete turn of the flow path 110 may include a fully enclosed ring or a 360 degree turn of a spiral. In a spiral configuration, the spiral may include a curve disposed in a single plane or a three-dimensional curve that extends longitudinally along an axis.

The elongate body 102 includes an absorbent material that may have liquid wicking performance. In some configurations, the elongate body 102 may include a liquid permeable cover layer having the same or a different material from the core material of the elongate body 102. The absorbent material may include cotton, organic cotton, rayon, viscose, lyocell, bamboo, foam, or a blend including any of the aforementioned materials. For example, the absorbent material may be a cotton-bamboo blend such as a 50-50 cotton-bamboo blend. With a cotton-bamboo blend, the bamboo component provides absorbency and antibacterial properties, while the cotton acts to "wick" a saturated product. Bamboo is also a sustainable material. As another example, the absorbent material may be a viscose blend such as a combination of Kelheim Galaxy® fiber and Kelheim Danufil® fiber. The viscose blend may include more Galaxy® fiber than Danufil® fiber, for example 70% Kelheim Galaxy® fiber and 30% Kelheim Danufil® fiber. The absorbent material may be a blend between viscose fibers and cotton.

Figure 3:
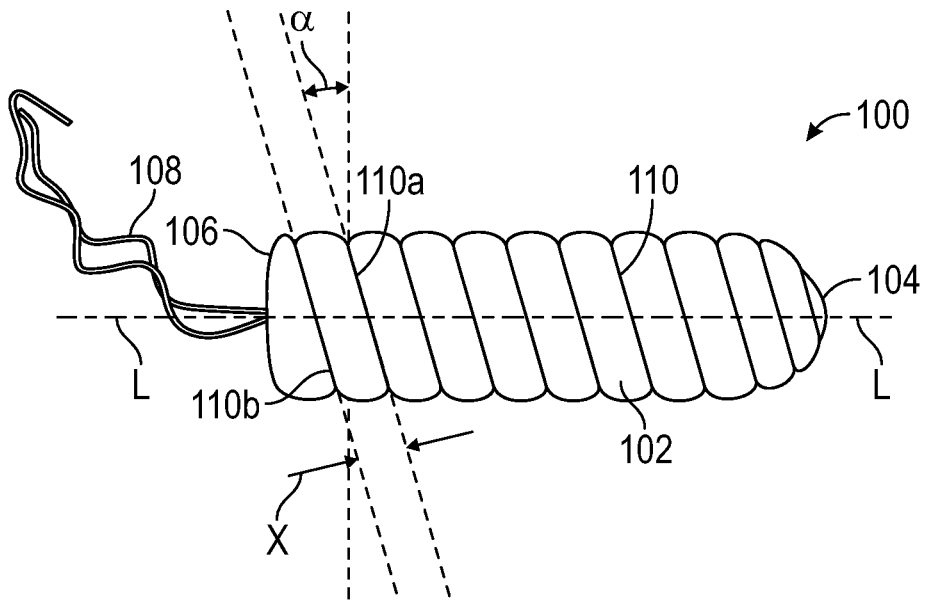
FIG. 3 illustrates a tampon with a right-handed spiral flow path.
Figure 4:
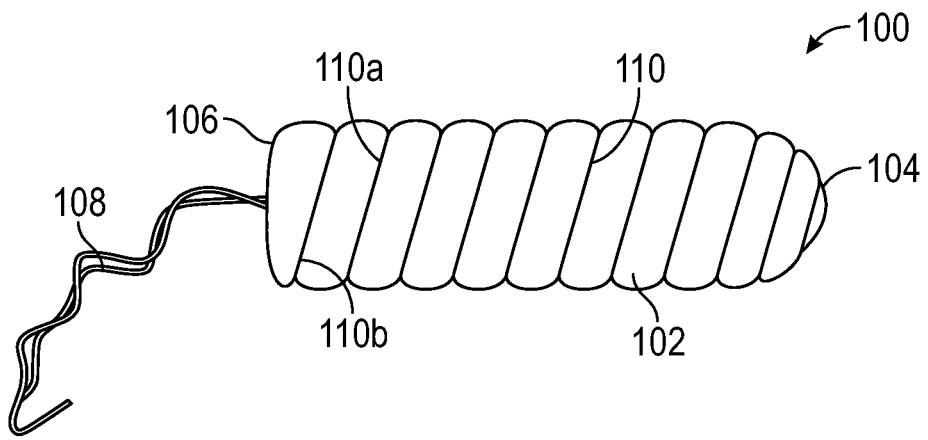
FIG. 4 illustrates a tampon with a left-handed spiral flow path.

As shown in FIG. 3, the flow path 110 may be a spiral flow path extending across a length of the elongate body 102. As illustrated, the flow path 110 is a right-handed spiral, but the flow path 110 may be a left-handed spiral (see FIG. 4). The flow path 110 begins at or near the first end 104 of the elongate body 102, for example within the rounded or tapered portion of the elongate body 102, and terminates at or near the second end 106 of the elongate body 102. The spiral flow path 110 begins with a free end and terminates at a free end. The spiral flow path 110 may be a single, continuous flow path along an external surface of the elongate body 102 with a single termination point at or near the second end 106 of the elongate body 102. The spiral flow path 110 increases the length of the flow path to provide a slower flow path for menses compared to a longitudinal flow path. The lengthened flow path gives the elongate body more time to absorb the menses and therefore reduces leakage. For a similar sized tampon having the same absorbent material, the spiral flow path increases total time to possible leakage by at least 10% to 20%.

Each turn of spiral flow path 110 rotates about the longitudinal axis L of the elongate body, such that each turn of the spiral flow path 110 is closer to latitudinal than longitudinal when viewed with insertion end 104 vertically above the removal end 102. At least one turn 110a, 110b of the spiral flow path 110 may be disposed at an angle α from horizontal where horizontal is perpendicular to the longitudinal axis L. The angle α can be less than or equal to about 60 degrees, less than or equal to about 40 degrees, or less than or equal to about 20 degrees. Each turn 110a, 110b of the spiral flow path may be disposed at the same angle α or the angles α may vary. Each turn 110a, 100b may be disposed at an angle that is at least about 45 degrees and/or less than or equal to about 90 degrees from the longitudinal axis L, for example between about 45 degrees and about 75 degrees, between about 50 degrees and about 80 degrees, or between about 60 degrees and about 90 degrees. The pitch x between successive turns 110a, 110b of the spiral flow path 110 may be less than or equal to about 20 mm, less than or equal to about 10 mm, or less than or equal to about 5 mm. In some configurations, a distance between any two points disposed 360 degrees apart along the spiral flow path 110 may be constant.

The spiral flow path 110 continually travels in a single or longitudinal direction from a single starting point at or near the insertion end 104 to a single terminating point at or near the removal end 106. When moving from the starting point to the terminating point, any selected location along the spiral flow path is closer to the removal end 106 of the elongate body 102 than any previous location between the starting point and the selected location. As the spiral flow path 110 travels toward the removal end 106, the spiral flow path 110 never turns back toward insertion end 104. This enables the menses to flow in a direction that is closer to latitudinal than longitudinal at any given segment of the flow path 110.

Figure 5:
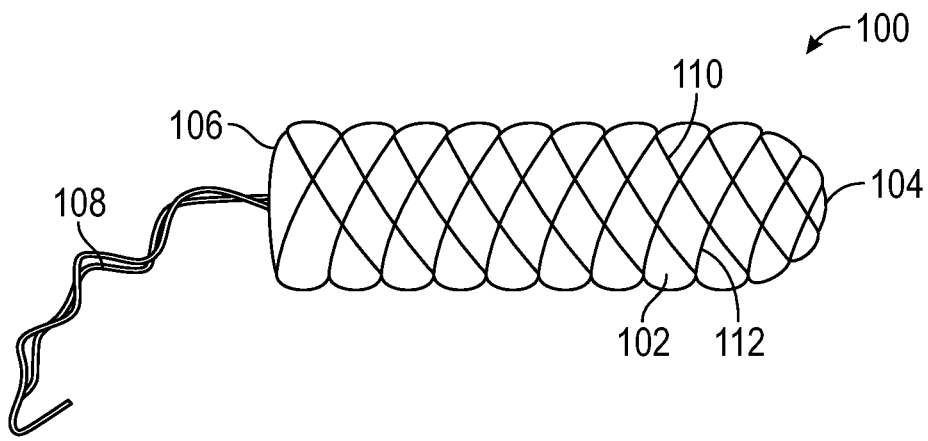
FIG. 5 illustrates a tampon with a double spiral flow path.

As explained above, the elongate body 102 may include more than one flow path. For example, as shown in FIG. 5, the elongate body 102 may include a first, right-handed spiral flow path 110 twisted together with a second, left-handed spiral flow path 112.

FIGS. 6A-6C illustrate a tampon 200 having an elongate body 202 with a first or insertion end 204 and a second or removal end 206. The elongate body 202 may include any of the absorbent materials described above. Although not shown, the tampon 200 may include a removal string extending from the removal end 206 of the elongate body 202. The tampon 200 may include any of the features described above with respect to the tampon 100.

The tampon 200 includes a spiral flow path 210 configured to direct a flow of menses along an outer surface of the elongate body 202. The spiral flow path 210 may be a groove, channel, or indentation that provides a recess in the outer surface of the elongate body 202. The spiral flow path 210 begins at or near the first end 204 of the elongate body 202 (see FIG. 6B) and terminates at or near the second end 206 of the elongate body 202 (see FIG. 6A). The spiral flow path 210 may provide a single, continuous recess terminating at a single location at the second end 206 of the elongate body 202. As shown in FIGS. 6A and 6B, there is only one spiral flow path 210 without any additional grooves, channels, indentations, or other flow paths.

When the tampon 200 sits within the vaginal cavity, the spiral flow path 210 enables the tampon to conform to the rugae along the vaginal walls to reduce the likelihood of displacement. For a 2.0 g tampon having a spiral flow path 210, the tampon 200 exhibits a tampon absorption rate of at least 9 g and has super absorbency rating according to the Syngyna test outlined by the Food and Drug Administration under 21 C.F.R. § 801.430 ("User labeling for menstrual tampons"). This means the tampon absorbed at least 9 g of fluid prior to the first drop of fluid leakage. Tampons having a spiral flow path 210 absorb at least about 3.75 grams of fluid per gram of dry absorbent material in the tampon, at least about 4.0 grams of fluid per gram of dry absorbent material in the tampon, or at least 4.25 grams of fluid per gram of dry absorbent material in the tampon. For example, tampons having the spiral flow path may absorb between about 4.0 grams to about 4.5 grams of fluid per gram of dry absorbent material according to the Syngyna test.

The spiral flow path 210 extends at least one complete turn around a circumference or perimeter of the elongate body 202. For example, the spiral flow path 210 may include at least about two complete turns (e.g., at least about three complete turns) and/or less than or equal to about ten complete turns, for example between about two complete turns and about four complete turns or between about three complete turns and about five complete turns. As shown in FIGS. 6A and 6B, the spiral flow path 210 extends about four complete turns around the circumference of the elongate body 202. However, the spiral flow path 210 may include a fewer or greater number of turns depending on the pitch x between successive turns of the spiral flow path 210. The pitch x may be less than or equal to about 20 mm, less than or equal to about 10 mm, or less than or equal to about 5 mm (see FIG. 6C). In some embodiments, the pitch x is between about 7.5 mm and about 10 mm or between about 5 mm and about 7.5 mm. The pitch x may be at least about 10% of a length of the elongate body 202 and/or less than or equal to about 40% of the length of the elongate body 202. In some embodiment, the pitch x is between about 10% and about 15% of a length of the elongate body 202 or between about 15% and about 20% of a length of the elongate body 202. The pitch x may be constant or varied along the length of the spiral flow path 210.

A depth d of the spiral flow path 210, measured from an outer surface of the elongate body 202 to an apex of the spiral flow path 210, is sufficiently shallow to maintain the integrity of the elongate body 202. For example, the depth d may be less than or equal to about 5 mm, for example less than or equal to about 3 mm. The depth d of the recess may be less than or equal to about 40% (e.g., 30%-40%, 20%-30%, 15%-25% and numerical values in between) of a width of the elongate body 202, for example less than or equal to about 25% (e.g., 20%-25%, 15%-20%, 10%-15% and numerical values in between) of a width of the elongate body 202. The depth d of the recess may be constant or varied along the length of the spiral flow path 210.

The width w at an opening of the spiral flow path 210 may be less than or equal to about 5 mm, for example less than or equal to about 2 mm. In some embodiments, the width is between about 1.5 mm and about 2.5 mm (e.g., 1.5-2.0 mm, 1.75-2.25 mm and numerical values within those ranges).

The width w may be less than or equal to about 15% of the length of the elongate body 202, for example less than or equal to about 10% of the length of the elongate body 202 (e.g., 10% to 15%, 7.5% to 12.5%, 5% to 10% and numerical values within those ranges). The width w at the opening of the spiral flow path 210 may be constant or varied along the length of the spiral flow path 210.

The spiral flow path 210 includes an inner surface 214. As illustrated, the spiral flow path 210 includes two inner surfaces 214 tapered toward an apex of the recess. However, in other configurations, the width w at the opening of the spiral flow path 210 may be the same or narrower than the opposite side of the spiral recess (e.g., at the most radially inward edge of the spiral flow path 210). For example, the two inner surfaces 214 may be parallel or diverge from each other. In other configurations, the inner surface 214 of the flow path 210 may be rounded such that the inner surface 214 has a concave profile when viewed in cross-section. The radius of curvature at the open side of the flow path 210 may be greater than, less than, or the same as the radius of curvature at the innermost edge of the flow path 210. The inner surface 214 and the outer surface of the elongate body 202 may form a sharp edge or a rounded edge. An inner surface 214 of the spiral flow path 210 may be disposed at an angle α from horizontal, measured perpendicular to the longitudinal axis L of the elongate body 202 (see FIG. 6C). The angle α may be less than or equal to about 40 degrees, less than or equal to about 30 degrees, less than or equal to about 20 degrees, less than or equal to about 15 degrees, or less than or equal to about 10 degrees. In some embodiments, the angle α is between 30 degrees and about 40 degrees, between about 25 degrees and about 35 degrees, between about 15 degrees and about 25 degrees and numerical values within those ranges. The angle α may be constant or varied along the length of the spiral flow path 210. Each turn of the spiral flow path 210 may be disposed at an angle that is between about 45 degrees and about degrees from the longitudinal axis L, for example between about 45 degrees and about 75 degrees, between about 50 degrees and about 80 degrees, or between about 60 degrees and about 90 degrees.

Each turn of the spiral flow path 210 may have a radius of curvature of less than or equal to about 10 mm, less than or equal to about 8 mm, or less than or equal to about 6 mm (e.g., 2-6 mm, 3-5 mm, 4-8 mm and numerical values within those ranges). The radius of curvature may be constant or varied along the length of the spiral flow path 210. The entire spiral flow path 210 may have a curvature without any corners or apexes forming a point.

With reference to FIGS. 7A-7D, another tampon 300 is shown. The tampon 300 resembles or is identical to the tampon 200 except as described below.

In addition to the spiral flow path 310, the elongate body 302 may have one or more secondary flow paths 316. For example, the elongate body 302 may include a plurality of secondary flow paths 316 spaced apart from each other around a circumference of the elongate body 302. Each secondary flow path 316 may cross successive turns of the spiral flow path 310. Each secondary flow path 316 may extend in a generally longitudinal direction or at least closer to the longitudinal direction than the turns of the spiral flow path 316. The secondary flow paths 316 facilitate tampon expansion, which can facilitate more even absorption. An under-expanded tampon may lead to premature leakage.

The secondary flow paths 316 may be grooves, channels, or indentations that form a recess in an outer surface of the elongate body 302. Each secondary flow path 316 may begin at or near the first end 304 of the elongate body 302 and terminate at or near the second end 306 of the elongate body 302. Each secondary flow path 316 may be circumferentially spaced apart by at least about 2 mm, at least about 4 mm, or at least about 6 mm (e.g. 2-4 mm, 3-5 mm, 4-6 mm and numerical values within those ranges). The space between successive secondary flow paths 316 may be constant or varied around the circumference of the elongate body 302.

A depth d' of the secondary flow path 316, measured from the outer surface of the elongate body 302 to an apex of the secondary flow path 316, may be the same or different from the depth d of the spiral flow path 310. For example, the depth d' may be less than or equal to about 5 mm or less than or equal to about 3 mm (e.g., 2-4 mm, 2.5-4.5 mm, 3-mm and numerical values within those ranges). The depth d' of the secondary flow path 316 may be less than or equal to about 40% of a width of the elongate body 302, for example less than or equal to about 25% of a width of the elongate body 302 (e.g., 15% to 25%, 20% to 30%, 25% to 35% and numerical values within those ranges). The depth d of the secondary flow path 316 may be constant or varied along a length of the spiral flow path 310.

The width w' at an opening of the secondary flow path 316 may be the same or different from the width w of the spiral flow path 310. For example, the width w' may be less than or equal to about 5 mm (e.g., 3-5 mm, 1-3 mm, 0.5-2 mm and numerical values within those ranges) or less than or equal to about 2 mm. The width w' may be less than or equal to about 10% (e.g., 8-10%, 6-8%, 3-6%, 1-5%, and numerical values within those ranges) of a circumference of the elongate body 302, for example less than or equal to about 5% of a circumference of the elongate body 302. The width w' at the opening of the secondary flow path 316 may be constant or varied along the length of the spiral flow path 310.

Figure 7A:
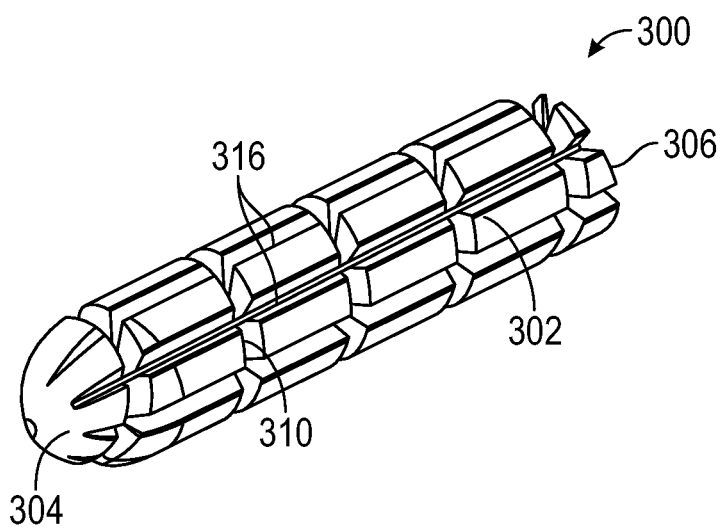
FIGS. 7A-7D illustrate a tampon having a spiral flow path and secondary flow paths crossing the spiral flow path.
Figure 7B:
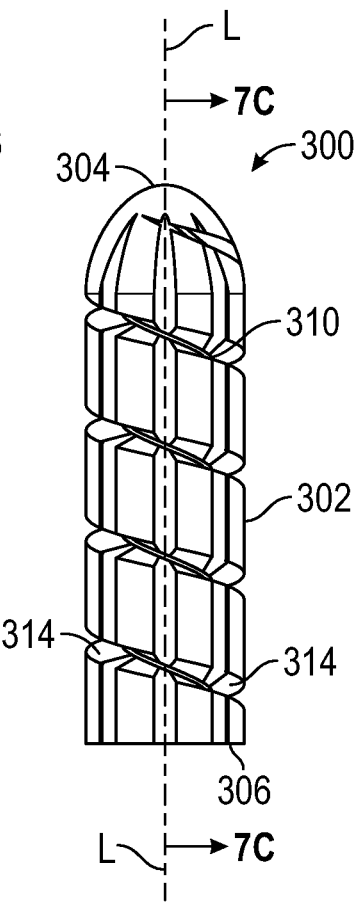
Figure 7C:
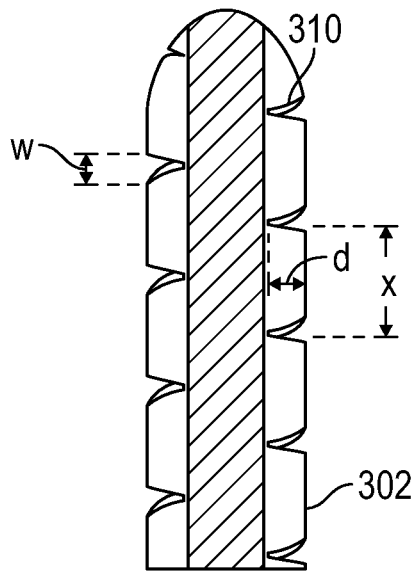
Figure 7D:
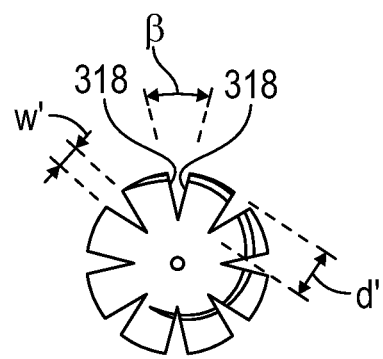

Each secondary flow path 316 may be defined by adjacent inner surfaces 318 (see FIG. 7D). An angle β between the adjacent inner surfaces 318 may be less than or equal to about 40 degrees, less than or equal to about 30 degrees, less than or equal to about 20 degrees, less than or equal to about 15 degrees, or less than or equal to about degrees. For example, the angle β may be between about 20 degrees and 25 degrees, between about 17.5 and 22.5 degrees, between about 15 degrees and 20 degrees and numerical values within those ranges. The angle β may be constant or varied along the length of the spiral flow path 310.

Figure 8A:
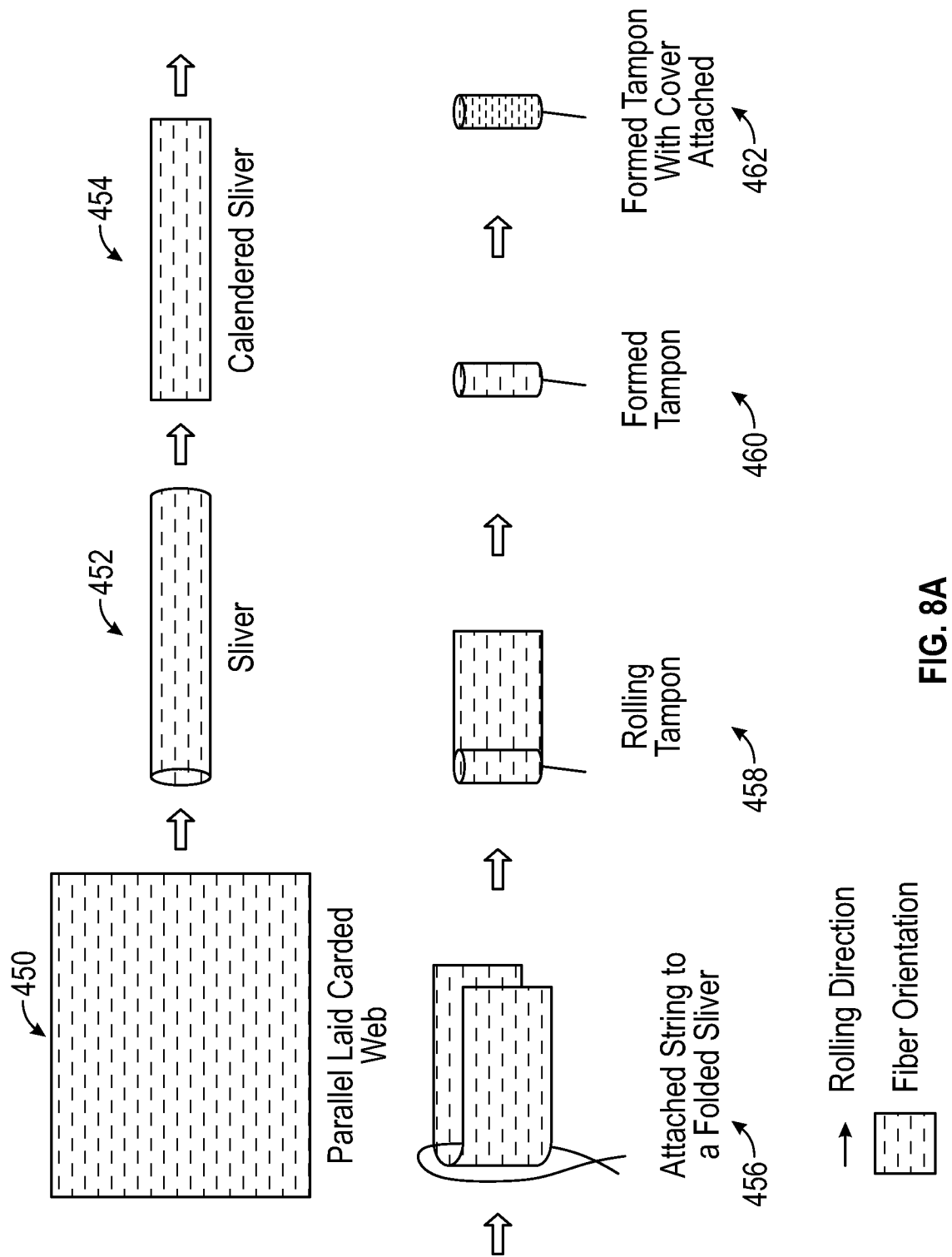
FIG. 8A illustrates a method of manufacturing a tampon.

FIG. 8A illustrates a method of manufacturing the tampons 100, 200, 300. Fibers of any material described herein can be carded into a web, for example a parallel laid web in which the fibers are oriented parallel to each other (step 450). The basis weight of the web may be at least about 20 g/m² and/or less than or equal to about 50 g/m², for example between about 20 g/m² and about 40 g/m² (e.g., 20-30 g/m², 25-35 g/m², 30-40 g/m² and numerical values within those ranges). After the web is formed, the web is passed through a can coiler sliver former (step 452). The sliver may then be densified using a cold calendaring process (step 454). A single tampon may include about 1.5 g to about 2.5 g of the calendared sliver, for example between about 1.9 g and 2.1 g. The calendared sliver may be folded so that a removal string may be applied to the sliver (step 456). The folded sliver may be rolled, for example in a swiss roll design, in the same direction as the orientation of the fibers (step 458) to form the tampon shown in step 460. The horizontally oriented fibers slow fluid flow in the longitudinal direction. In some embodiments, the tampon may be rolled such that a central core of the elongate body is more dense than an outer portion of the elongate body. In other embodiments, the density of the elongate body may be constant throughout.

Optionally, a cover layer may be provided over the elongate body (step 462). The cover layer may be a layer of nonwoven material, which may be the same or different from the core material. The cover layer may be a layer of carded, nonwoven material or a spunbound material. The cover layer may have a lower basis weight than the core. For example, the basis weight of the cover layer may be less than or equal to about 20 g/m$^2$ or less than or equal to about 15 g/m$^2$ (e.g., 7.5-12.5 g/m$^2$, 10-15 g/m$^2$, 12.5-17.5 g/m$^2$ and numerical values within those ranges). The cover layer may be bonded to the absorbent core of the elongate body, for example thermally bonded using a hot knife.

Although a particular manufacturing method is described with respect to FIG. 8A, the tampons described herein may be manufactured using other methods. For example, after the elongate body is formed, the elongate body may be twisted to form the external spiral flow path having at least one complete turn.

Figure 8B:
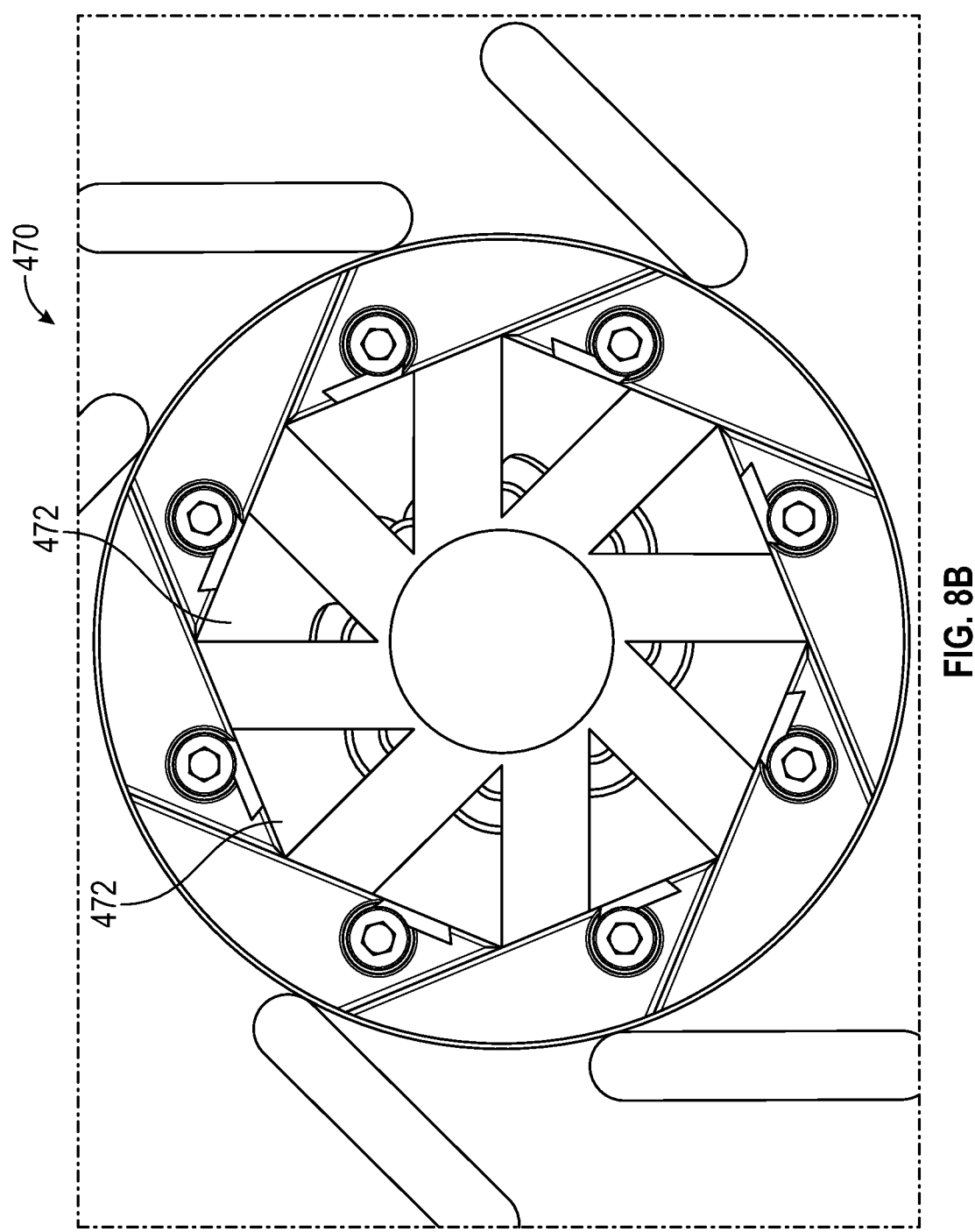
FIGS. 8B and 8C illustrate a mold that may be used to manufacture a tampon.
Figure 8C:
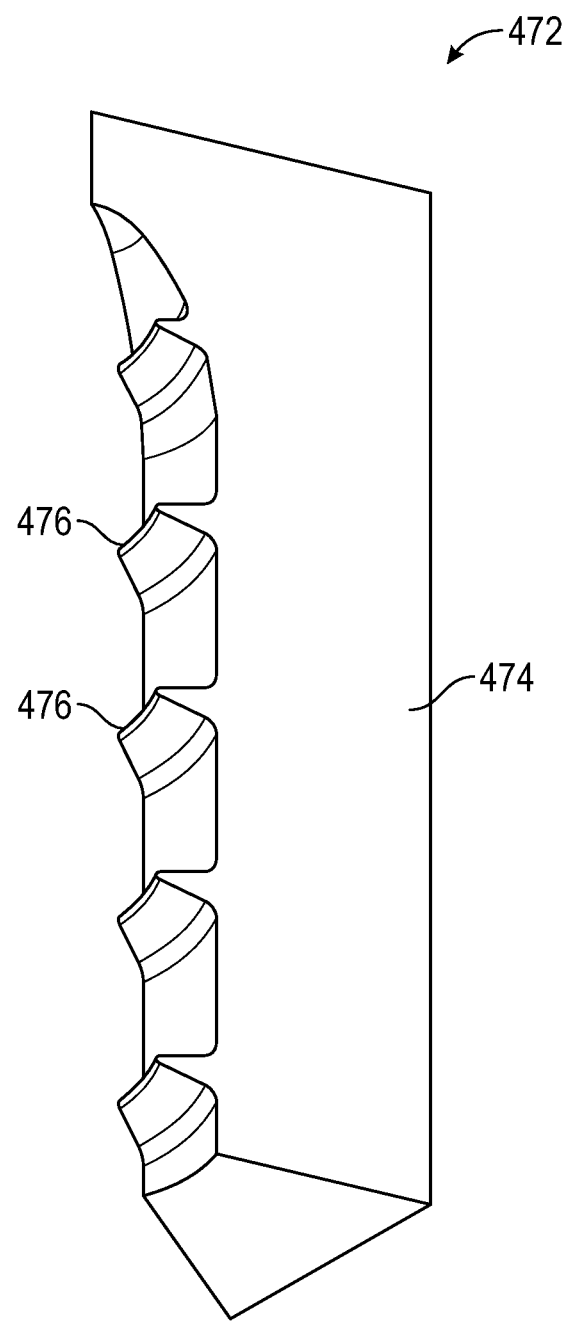

As described above, the elongate body may include one or more flow paths in the outer surface of the elongate body. The flow paths may be molded into the outer surface of the elongate body, for example using a radial compression mold. The mold forms grooves, channels, or indentations that form recesses in the outer surface of the elongate body. The localized compression along the flow path adds more surface area and friction as fluid meets the flow path, thereby slowing the rate of fluid flow in the longitudinal direction. The slower fluid flow provides more time for the elongate body to absorb fluid, promotes full saturation of the tampon, and delays possible leakage. FIG. 8B provides an example of a compression mold 470 including one or more mold segments 472 disposed circumferentially around the mold 470. Each mold segment 472 may be tapered toward a center of the mold 470. Each segment 472 may span between 30 degrees and 180 degrees of the elongate body, for example between 45 degrees and 90 degrees of the elongate body. In use, the formed tampon may be disposed at the center of the one or more mold segments 472. As the one or more mold segments 472 move radially inward toward the elongate body of the tampon, the flow path is formed in the outer surface of the elongate body. This compression process may be manual or automated. FIG. 8C illustrates a single mold segment 472. As illustrated, the mold segment 472 includes a body portion 474 and one or more projections 476 projecting from the body portion 474. The one or more projections 476 form a negative of at least a partial segment of the flow path to be created on the elongate body. Thus, the projections 476 may have dimensions similar to those described with respect to the flow path 210 above. When all the mold segments 472 are combined, there is a complete negative of the flow path to be created on the elongate body.

Figure 9:
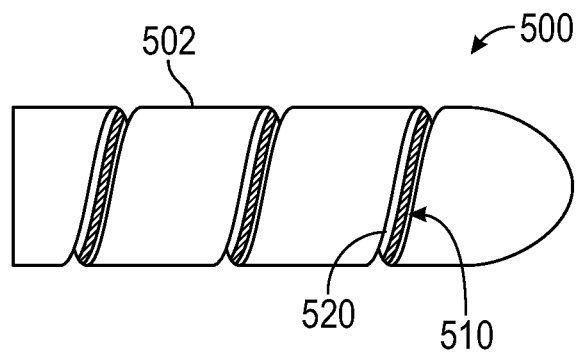
FIG. 9 illustrates another tampon having a spiral flow path.

FIG. 9 illustrates a tampon 500 that resembles or is identical to tampons 200, 300 except as described below. As shown in FIG. 9, the elongate body 502 includes a spiral flow path 510 similar to the spiral flow paths 210, 310. In this configuration, the elongate body 502 includes a thread 520 extending around the elongate body 502 to form the spiral flow path 510. The thread 520 compresses the outer surface of the elongate body 502 to form a spiral recess in the outer surface of the elongate body 502. The thread 520 may include a same or different material from the absorbent material of the elongate body 502 or the removal string. For example, the thread 520 may include cotton, polyester, polypropylene, or a blend including any of the aforementioned materials. A hydrophilic or hydrophobic coating may be applied to the thread 520. The thread 520 may be a single fiber or braided from multiple fibers. The thread 520 may be a filament, ribbon, wire, or any other string-like structure.

The elongate body 502 of the tampon 500 may be formed using the method shown in FIG. 8A. After the elongate body 502 is formed, the thread 520 may be fastened around the elongate body 502 to compress the outer surface of the elongate body 502 and form the spiral flow path 510. The thread 520 may be woven into the spiral orientation, for example using a rotating tool. The thread 520 may be chemically, thermally, or mechanically bonded to the outer surface of the elongate body 502. At least the ends of the thread 520 may be bonded to the elongate body 502. In some methods, the thread 520 may be bonded to the elongate body 502 along an entire length of the thread 520.

Figure 10:
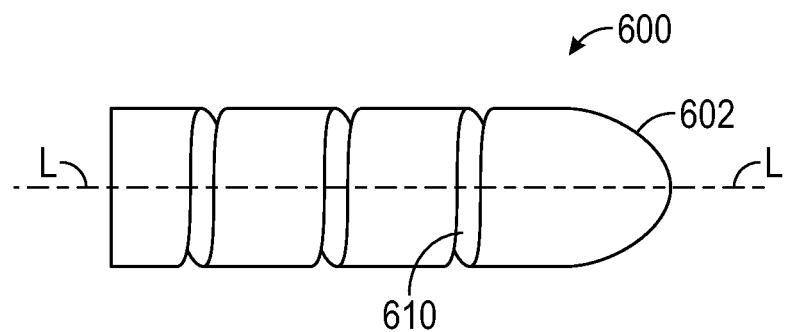
FIG. 10 illustrates a tampon having latitudinal flow paths.

FIG. 10 illustrates a tampon 600 that may include any features of the above-described tampons. The tampon 600 includes an elongate body 602 and one or more flow paths 610. Each of the one or more flow paths 610 may be a groove, channel, or indentation that forms a recess in an outer surface of the elongate body 602. Unlike the spiral configurations described above, each flow path 610 may form a fully enclosed ring, such as an annular ring disposed in a single plane. For example, as shown in FIG. 10, each flow path 610 may be disposed in a single plane that is perpendicular to the longitudinal axis L of the elongate body 602. However, in other configurations, each flow path 610 may be disposed at an oblique angle relative to the longitudinal axis L, for example at an angle that is less than or equal to about 60 degrees, less than or equal to about 40 degrees, or less than or equal to about degrees relative to the longitudinal axis L (e.g., 50-60 degrees, 45-55 degrees, 40-50 degrees, 35-45 degrees and numerical values within those ranges). In some configurations, the flow path 610 may be disposed at an angle that is between about 45 degrees and about 90 degrees from the longitudinal axis L, for example between about 45 degrees and about 75 degrees, between about 50 degrees and about 80 degrees, or between about 60 degrees and about 90 degrees.

The elongate body 602 may include at least two flow paths 610 and/or less than or equal to ten flow paths 610, for example between three flow paths 610 and five flow paths 610. However, the elongate body 602 may include a fewer or greater number of flow paths 610 depending on the distance between successive flow paths 610. Successive flow paths 610 may be separated by a distance of less than or equal to about 20 mm, less than or equal to about 10 mm, or less than or equal to about 5 mm. In some embodiments, the distance is between about 7.5 mm and 10 mm or between about 5 mm and about 7.5 mm. The distance between successive flow paths 610 may be at least about 10% of a length of the elongate body 602 and/or less than or equal to about 40% of a length of the elongate body 602. In some embodiment, the distance is between about 10% and 15% of a length of the elongate body 602 or between about 15% and about 20% of a length of the elongate body 602. The distance between successive flow paths 610 may be constant or varied along a length of the elongate body 602.

Figure 11:
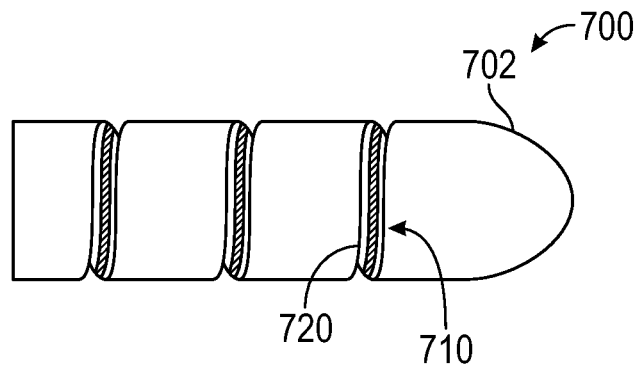
FIG. 11 illustrates another tampon having latitudinal flow paths.

FIG. 11 illustrates a tampon 700 that resembles or is identical to the tampon 600 except as described below. As shown in FIG. 11, the elongate body 702 includes a plurality of latitudinal flow paths 710 similar to the flow paths 610. In this configuration, the elongate body 702 includes a plurality of threads 720 extending around the elongate body 702 to form the one or more flow paths 710. The plurality of threads 720 compress the outer surface of the elongate body 702 to form the recessed flow paths 710.

For a 2.0 g tampon having the latitudinal flow paths 610, 710, the tampons 600, 700 exhibit a tampon absorption rate of at least 9 g and has super absorbency rating according to the Syngyna test. This means the tampon absorb at least 9 g of fluid prior to the first drop of fluid leakage. Tampons 600, 700 having a plurality of latitudinal flow paths 610, 710 absorb at least about 3.75 grams of fluid per gram of dry absorbent material in the tampon or at least about 4.0 grams of fluid per gram of dry absorbent material in the tampon. For example, tampons 600, 700 having a plurality of latitudinal flow paths 610, 710 may absorb between about 3.75 grams and about 4.0 grams or between about 4.0 grams and about 4.25 grams of fluid per gram of dry absorbent material according to the Syngyna test. For a similar sized tampon having the same absorbent material, the latitudinal flow paths 610, 710 increase total time to possible leakage by at least 5% to 35%.

As mentioned above, in addition, or in alternative to, the one or more flow paths disposed in the outer surface of the elongate body, the tampon may include one or more flow paths disposed within or internal of the elongate body to direct a flow of menses through the elongate body. The internal flow paths are not visible from an exterior of the tampon. The internal flow paths lengthen the total flow path, thus providing more time for the elongate body to absorb the menses and reducing the likelihood of leakage.

Figure 12A:
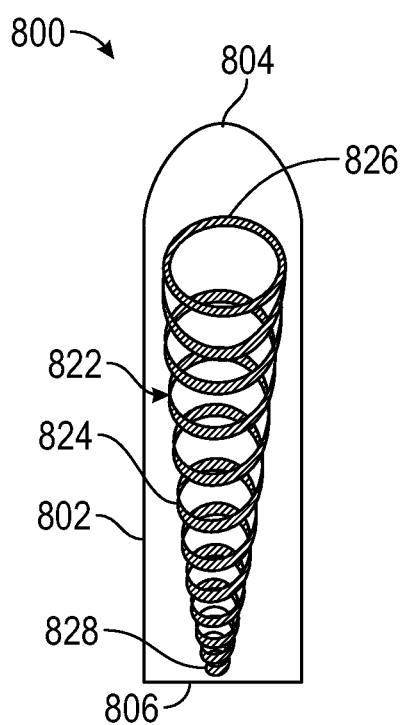
FIGS. 12A and 12B illustrate a tampon having an internal spiral flow path.

For example, as shown in FIG. 12A, the tampon 800 includes an internal flow path 822 positioned within the elongate body 802. The internal flow path 822 may provide a single, continuous spiral along at least a partial length or substantially the entire length of the elongate body 802. The internal flow path 822 includes a first end 826 positioned at or near the first end 804 of the elongate body 802 and a second end 828 that terminates at or near the second end 806 of the elongate body 802. As shown in FIG. 12A, there is only one internal flow path 822 without any additional internal flow paths.

The internal flow path 822 may include any of the features described above with respect to the spiral flow path 210. The internal flow path 822 extends at least one complete turn within the elongate body 802. Successive turns of the internal flow path 822 may have the same or different radius. As shown in FIG. 12A, the radius of the turns varies along a length of the internal flow path 822. A first radius of a turn at the first end 826 of the internal flow path 822 may be greater than a second radius of a turn at the second end 828 of the internal flow path 822.

The internal flow path 822 may be formed by a thread 824 extending through the elongate body 802. The thread 824 may include any of the properties of the thread 520 described above with respect to the tampon 500. The thread 824 may be continuous with or separate from the removal string 808.

Figure 12B:
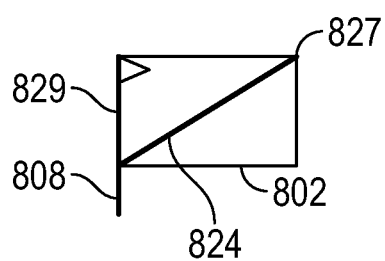

The elongate body 802 may be formed using a similar method to that shown in FIG. 8A. However, after the removal string is provided (see step 456), the thread 824 is provided to a surface of the sliver that will be internal of the elongate body 802. As shown in FIG. 12B, a single thread 824 is positioned diagonally across the folded sliver. The thread 824 may be bonded to the folded sliver or freely positioned on the folded sliver. The thread 824 may extend from a first location at or near a first corner 829, formed by the folded edge of the sliver and the edge that will form the second end 806 of the elongate body 802, toward a second location at or near a second corner 827, formed by the free edges of the sliver and the edge that will form the first end 804 of the elongate body 802. After the thread 824 is provided, the folded sliver may be rolled in the direction of the arrow, similar to step 458 of FIG. 8A.

Figure 13A:
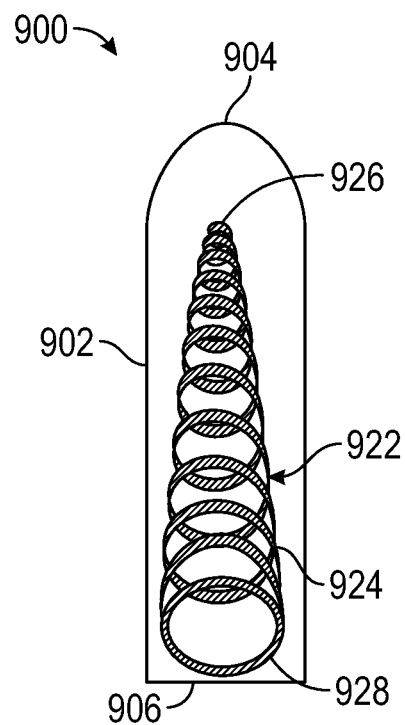
FIGS. 13A and 13B illustrate another tampon having an internal spiral flow path.

FIG. 13A illustrates a tampon 900 that resembles or is identical to the tampon 800 except as described below. As shown in FIG. 13A, the internal flow path 922 includes a first end 926 positioned at or near the first end 904 of the elongate body 902 and a second end 928 positioned at or near the second end 906 of the elongate body 902. A first radius of a turn at the first end 926 of the internal flow path 922 may be smaller than a second radius of a turn at the second end 928 of the internal flow path 922.

Figure 13B:
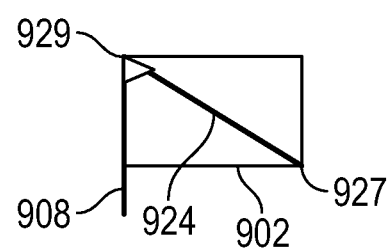

The tampon 900 may be formed using the same method described above with respect to the tampon 800 except that the thread 924 is applied to the folded sliver in the opposite direction. As shown in FIG. 13B, a single thread 924 is positioned diagonally across the folded sliver. The thread 924 may extend from a first location at or near a first corner 929, formed by the folded edge of the sliver and the edge that will form the first end 904 of the elongate body 902, toward a second location at or near a second corner 927, formed by the free edges of the sliver and the edge that will form the second end 906 of the elongate body 902. The thread 924 may be continuous with or separate from the removal string 908.

For a 2.0 g tampon having the internal flow path 822, 922, the tampon 800, 900 exhibits a tampon absorption rate of at least 8.5 g, or at least 9.0 g, according to the Syngyna test. Tampons 800, 900 having the internal flow path 822, 922 absorb at least about 3.75 grams of fluid per gram of dry absorbent material in the tampon or at least about 4.0 grams of fluid per gram of dry absorbent material in the tampon. For example, tampons 800, 900 having an internal flow path 822, 922 may absorb between about 3.75 grams and about 4.0 grams or between about 4.0 grams and about 4.25 grams of fluid per gram of dry absorbent material according to the Syngyna test. For a similar sized tampon having the same absorbent material, the internal flow path 822, 922 increases total time to possible leakage by at least 5% to 25%.

Figure 14A:
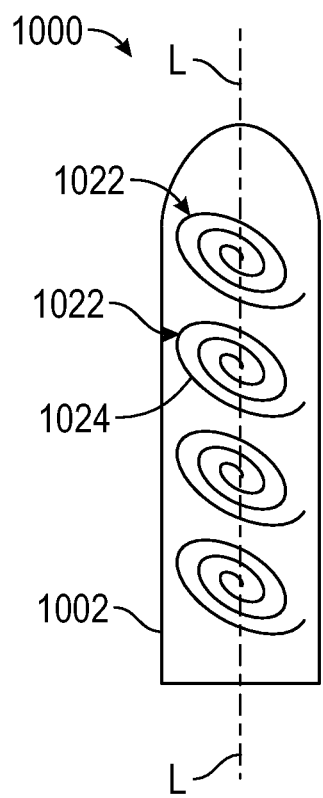
FIGS. 14A and 14B illustrate a tampon having a plurality of internal spiral flow paths.
Figure 14B:
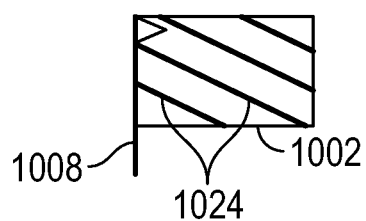
Figure 15B:
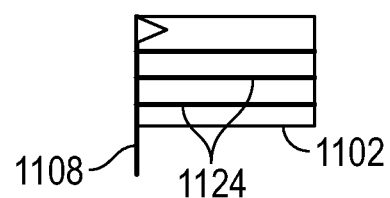

FIGS. 14A and 14B illustrate a tampon 1000 with a different internal flow path configuration. As shown in FIG. 14A, the tampon 1000 includes an elongate body 1002 with one or more internal flow paths 1022 positioned within the elongate body 1002.

Each flow path 1022 may be disposed within a single plane and at an oblique angle relative to a longitudinal axis L of elongate body 1002. As shown in FIG. 14A, the elongate body 1002 includes a plurality of internal flow paths 1022 longitudinally spaced apart along a length of the elongate body 1002. For example, the elongate body 1002 may include at least two internal flow paths 1022 and/or less than or equal to ten internal flow paths 1022, for example between three internal flow paths 1022 and five internal flow paths 1022. Successive internal flow paths 1022 may be separated by a distance that is less than or equal to about 30 mm, less than or equal to about 20 mm, less than or equal to about 10 mm, or less than or equal to about 5 mm. In some embodiments, the distance is between about 7.5 mm and about 10 mm or between about 5 mm and about 7.5 mm. The distance between successive internal flow paths 1022 may be at least about 10% of a length of the elongate body 1002 and/or less than or equal to about 40% of a length of the elongate body 202. In some embodiment, the distance is between about 10% and about 15% of a length of the elongate body 1002 or between about 15% and about 20% of a length of the elongate body 1002. The distance between successive internal flow paths 1022 may be constant or varied along a length of the elongate body 1002.

Each internal flow path 1022 may be disposed at a same or different angle relative to the longitudinal axis L of the elongate body 1022. For example, each internal flow path 1022 may be disposed relative to the longitudinal axis L at an angle θ that is less than or equal to about 60 degrees, for example between about 20 degrees and about 45 degrees (e.g., 20-30 degrees, 25-35 degrees, 30-40 degrees and numerical values within those ranges). Successive flow paths 1022 may be parallel to each other.

Each of the internal flow paths 1022 may be formed by a thread 1024 spiraling around a single point within the elongate body 1002. The spiraling thread includes at least one complete turn. The threads 1024 may include any of the properties of the thread 520 described above with respect to the tampon 500.

The elongate body 1002 may be formed using a similar method to that shown in FIG. 8A. However, after the removal string is provided (see step 456) one or more threads 1024 are provided to a surface of the sliver that will be internal of the elongate body 1002. As shown in FIG. 14B, a plurality of threads 1024 are positioned diagonally across the folded sliver and parallel to each other. Each thread 1024 begins at a first location closer to the edge of the sliver that will form the first end 1004 of the elongate body 1002 than the second end 1006 of the elongate body 1002 and terminates at a second location closer to the edge of the sliver that will form the second end 1006 of the elongate body 1002 than the first end 1004 of the elongate body 1002. The threads 1024 are provided at an angle that is dependent on the desired angle θ of the flow path 1022 relative to the longitudinal axis L of the elongate body 1002. The threads 1024 may be bonded to the folded sliver or freely positioned on the folded sliver. After the threads 1024 are provided, the folded sliver may be rolled in the direction of the arrow, similar to step 458 of FIG. 8A.

Although not shown, the flow paths 1022 may be angled in the opposite direction. In the opposite configuration, each thread 1024 begins at a first location closer to the edge of the sliver that will form the second end 1006 of the elongate body 1002 than the first end 1004 of the elongate body 1002 and terminates at a second location closer to the edge of the sliver that will form the first end 1004 of the elongate body 1002 than the second end 1006 of the elongate body 1002.

Figure 15A:
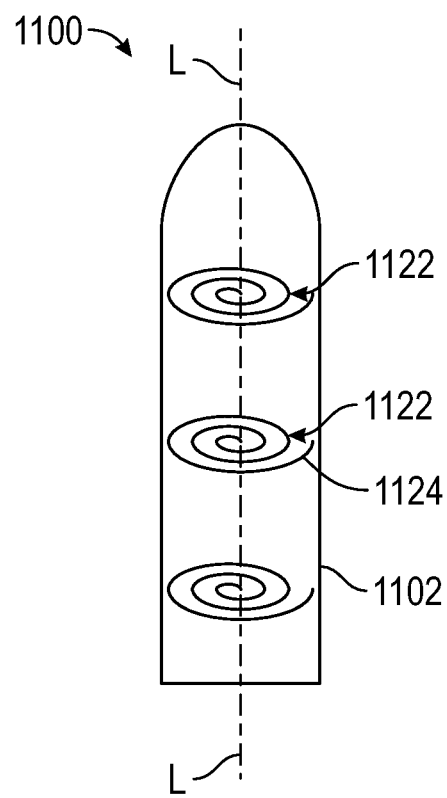
FIGS. 15A and 15B illustrate another tampon having a plurality of internal spiral flow paths.

FIG. 15A illustrates a tampon 1100 that resembles or is identical to the tampon 1000 except as described below. As shown in FIG. 15A, each of the plurality of internal flow paths 1122 lies in a plane perpendicular to the longitudinal axis L. The tampon 1100 may be formed using the same method described above with respect to the tampon 1000 except that the one or more threads 1124 are applied to the folded sliver in a latitudinal direction. The plurality of threads 1124 may be provided in the same direction as the fibers of the carded web.

For a 2.0 g tampon having the internal flow path 1022, 1122, the tampon 1000, 1100 absorb at least about 3.5 grams of fluid per gram of dry absorbent material in the tampon or at least about 3.75 grams of fluid per gram of dry absorbent material in the tampon. For example, tampons 1000, 1100 having internal flow paths 1022, 1122 may absorb between about 3.5 grams and about 3.75 grams or between about 3.75 grams and about 4.0 grams of fluid per gram of dry absorbent material according to the Syngyna test. For a similar sized tampon having the same absorbent material, the internal flow paths 1022, 1122 increases total time to possible leakage by at least 5% to 15%.

Figure 16A:
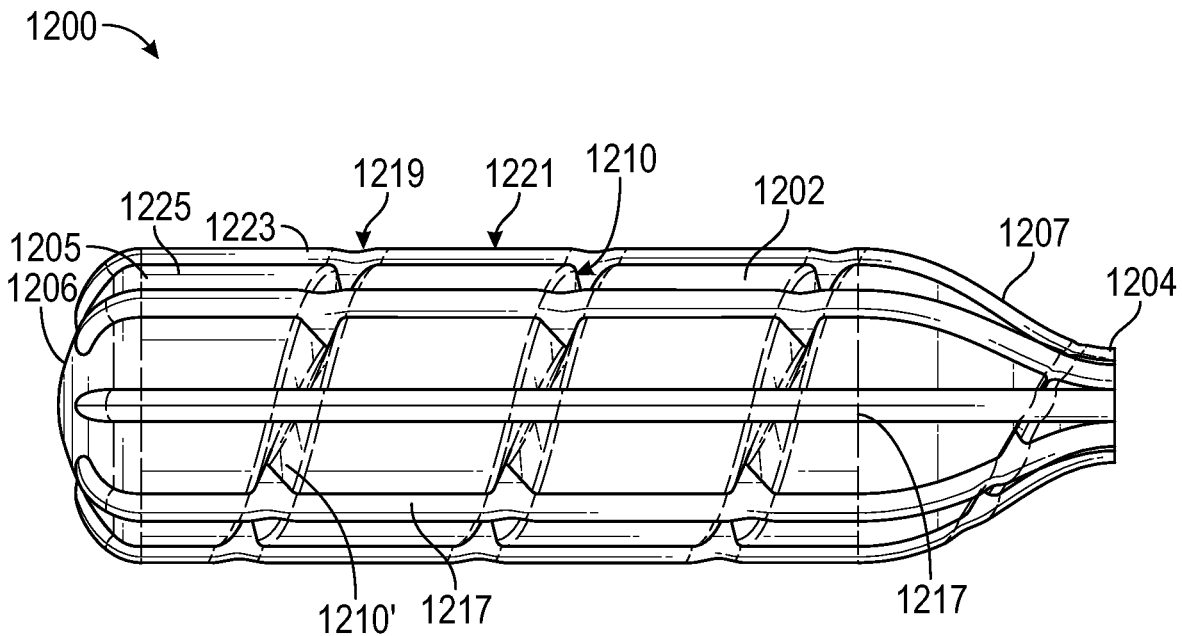
FIGS. 16A and 16B illustrate a tampon having longitudinal ribs.
Figure 16B:
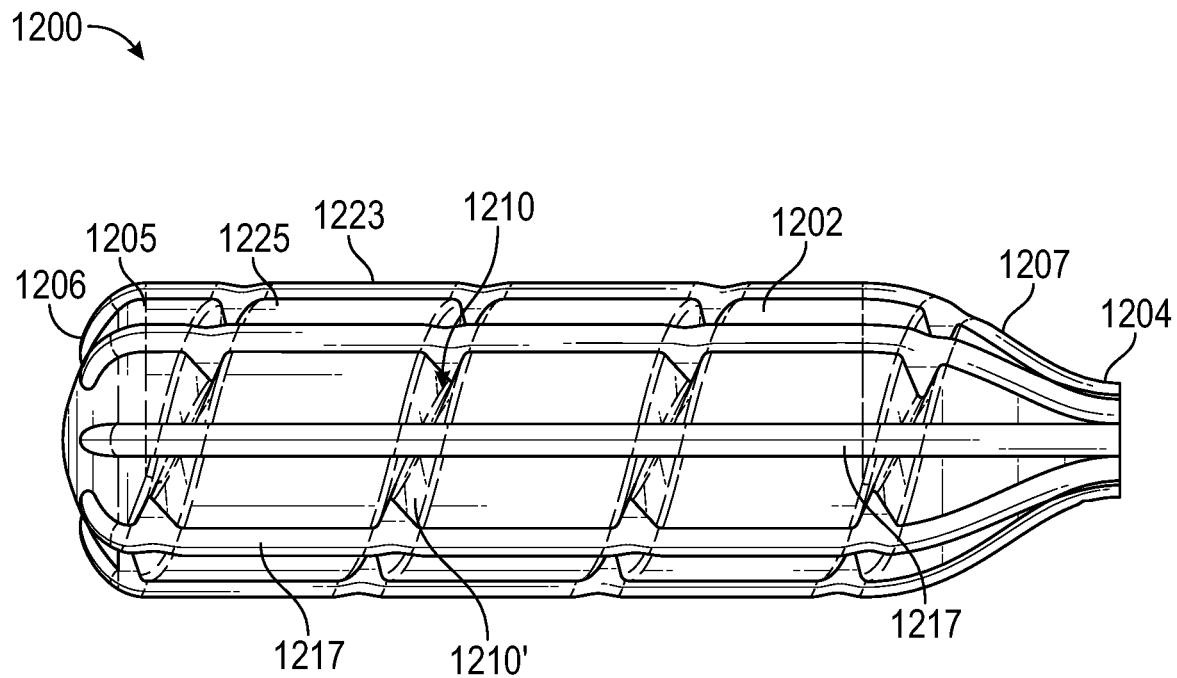

FIGS. 16A and 16B illustrate front and rear views of another tampon 1200. The elongate body 1202 may include one or more longitudinal ribs 1217 crossing a flow path 1210. The flow path 1210 may include any of the features described above with respect to the flow path 210. For example, the flow path 1210 may be shaped to redirect fluid at least partially in a horizontal direction to slow the time it takes for the fluid to reach the second end 1206 of the tampon and subsequently leak. The flow path 1210 may include a spiral shape to redirect fluid around a circumference of the elongate body 1202 rather than allowing the fluid to flow straight down from the first end 1204 to the second end 1206 of the elongate body 1202. The flow path 1210 may be continuous about the elongate body 1202 of the tampon 1200 except for the longitudinal ribs 1217. In some embodiments, the tampon 1200 only has a spiral, recessed flow path 1210 and longitudinal ribs 1217 with no other recessed flow paths or ribs extending in other directions. But in other embodiments, the longitudinal ribs 1217 may provide alone or in combination with any shape or number of flow paths.

The direction of fluid flow along flow path 1210 may be dependent on at least the shape and orientation of the flow path 1210. In some embodiments, fluid that enters the flow path 1210 may flow generally unidirectionally along the flow path 1210 and toward the second end 1206. In other embodiments, fluid that enters the flow path 1210 may flow in more than one direction along the flow path 1210. For example, fluid may flow bidirectionally along the flow path 1210. For a spiral flow path 1210, fluid may flow in both the clockwise and counterclockwise direction along the flow path 1210.

Fluid that approaches the elongate body 1202 from the first end 1204 may enter the flow path 1210 at or near an entry end of the flow path 1210. At least some excess fluid may bypass at least a portion of the flow path 1210 and flow in a longitudinal direction toward the second end 1206. The excess fluid may enter the flow path 1210 at a later portion of the flow path 1210, for example beyond the entry end or first turn of the flow path 1210. The excess fluid that enters at a later portion of the flow path 1210 may travel unidirectionally or bidirectionally along the flow path 1210 depending on the shape and orientation of the flow path 1210. Whether unidirectional or bidirectional, flow along the flow path 1210 may be non-vertical or closer to horizontal compared to flow in the longitudinal direction. This slows the time it takes for the fluid to reach the second end 1206.

The elongate body 1202 has an outer surface 1225. The longitudinal ribs 1217 protrude from the outer surface 1225, while the flow path 1210 is recessed from the outer surface 1225. The outer surface 1225 may extend longitudinally between successive turns 1210 of the flow path 1210 and/or circumferentially between adjacent ribs 1217. Sections of the flow path 1210 may be positioned between adjacent ribs 1217. Each section of the flow path 1210 may be non-parallel to the adjacent ribs 1217. The sections of the flow path 1210 may extend at an oblique angle relative to the ribs 1217.

The longitudinal ribs 1217 maximize tampon expansion when saturated, which prevents premature leakage caused by an under-expanded tampon. The longitudinal ribs 1217 may have a fibrous construction that quickly expands and relaxes upon release, such that the longitudinal ribs 1217 do not substantially affect fluid flow through the flow path 1210. When the tampon 1200 comes into contact with fluid, the fluid can follow the flow path 1210 substantially uninterrupted. The longitudinal ribs 1217 do not obstruct the slowing effects of the flow path 1210.

The plurality of longitudinal ribs 1217 may be spaced apart from each other around a circumference of the elongate body 1202. The tampon 1200 may include at least two longitudinal ribs 1217, at least four longitudinal ribs 1217, at least six longitudinal ribs 1217, or at least eight longitudinal ribs 1217. Each longitudinal rib 1217 may extend in a generally longitudinal direction or at least closer to the longitudinal direction than the turns of the flow path 1210. As illustrated, the longitudinal ribs 1217 are generally straight and aligned with the longitudinal axis of the elongate body, but in other configurations may include ribs that are angled, waved, curved, or otherwise shaped relative to the longitudinal axis of the elongate body.

The flow path 1210 may be a continuous spiral flow path intersected by the longitudinal ribs 1217. Each longitudinal rib 1217 may extend into the flow path 1210 at locations 1219 where the longitudinal rib 1217 crosses the flow path 1210. Viewed another way, the elongate body 1202 may include a plurality of flow path segments 1210' separated by the longitudinal ribs 1217. The plurality of flow path segments 1210' generally direct fluid in a spiral flow path around the elongate body 1202. Circumferentially adjacent flow path segments 1210' may be separated by one of the ribs 1217. The flow path segments 1210' between any two adjacent ribs 1217 may be longitudinally spaced apart from each other.

Each longitudinal rib 1217 may be integral with or joined to a recessed surface of the flow path 1210. The outer edge 1223 of the longitudinal rib 1217 may extend radially outward of an outer surface 1225 of the elongate body 1202 along a majority of or substantially the entire length of the longitudinal rib 1217. An outer edge 1223 of the longitudinal rib 1217 may be recessed at a first location 1219 where the longitudinal rib 1217 crosses the flow path 1210 compared to a second location 1221 between successive turns of the flow path 1210. In other configurations, an outer edge 1223 of the longitudinal rib 1217 may be generally straight or smooth along a majority of or entire length of the longitudinal rib 1217, without any recesses along the outer edge 1223 of the longitudinal rib 1217.

Each longitudinal rib 1217 may begin at or be spaced apart from the first end 1204 of the elongate body 1202. The longitudinal ribs 1217 may converge toward each other at or near the first end 1204 of the tampon 1200. For example, the longitudinal ribs 1217 may follow a tapered or conical portion 1207 of the first end 1204. The longitudinal ribs 1217 may be bunched or compressed together at the first end 1204 to form the insertion tip of the tampon 1200. The bunched insertion tip may include a reduced diameter compared to the remainder of the tampon. For example, the bunched insertion tip may extend from the tapered portion 1207 of the tampon 1200. The convergence of the longitudinal ribs 1217 at the insertion tip guides fluid toward the core and traps fluid in the absorbent internal fibers within the elongate body 1202. This prevents fluid from running down the outer surface 1225 of the tampon 1200.

Each longitudinal rib 1217 may terminate at or be spaced apart from the second end 1206 of the elongate body 1202. Each longitudinal rib 1217 may terminate at or near a transition 1205 between a lateral surface and a bottom surface of the tampon 1200. For example, the longitudinal 1217 may extend around the transition 1205 and across at least a portion of the bottom surface of the tampon 1200. Each rib 1217 may extend at least a majority or substantially the entire length of the elongate body 1202.

A thickness of each longitudinal rib 1217, measured in a radial direction, may be general constant along a length of the longitudinal rib 1210. In other configurations, the thickness of the longitudinal rib 1217 may vary along the length of the longitudinal rib 1217. For example, the thickness of the longitudinal rib 1217 may be thicker at the first location 1219 where the longitudinal rib 1217 crosses the flow path 1210 compared to the second location 1221 between successive turns of the flow path 1210.

Upon expansion and/or saturation of the tampon, the elongate body 1202 may expand toward the outer edge 1223 of the longitudinal ribs 1217, thereby reducing a thickness of the longitudinal ribs 1217 projecting from the outer surface 1225. In some configurations, the outer surface 1225 of the elongate body 1202 may become flush with the plurality of longitudinal ribs 1217. For example, the tampon 1200 may include a first expanded state in which the longitudinal ribs 1217 have a first thickness, and a second expanded state in which the longitudinal ribs 1217 have a second thickness, different from the first thickness. In some configurations, the second thickness may be negligible or zero with the longitudinal ribs 1217 no longer being visible or present. In some configurations, the elongate body 1202 may not expand beyond the outer edges 1223 of the longitudinal ribs 1217. The longitudinal ribs 1217 may preserve a maximum circumference of the tampon 1200, while making portions of the tampon 1200 between the longitudinal ribs 1217 smaller for insertion. As the tampon 1200 expands, the flow path 1210 may become more prominent, for example, a width of the flow path 1210 may increase.

The longitudinal ribs 1217 may be circumferentially spaced apart by at least about 2 mm, at least about 4 mm, or at least about 6 mm (e.g. 2-4 mm, 3-5 mm, 4-6 mm and numerical values within those ranges). The space between successive longitudinal ribs 1217 may be constant or varied around the circumference of the elongate body 1202. Each rib 1217 may extend from the outer surface 1225 of the elongate body 1202 by no more than about 5 mm or no more than about 3 mm (e.g., 2-4 mm, 2.5-4.5 mm, 3-5 mm and numerical values within those ranges). The width of each rib 1217, measured in a circumferential direction, may be less than or equal to about 5 mm (e.g., 3-5 mm, 1-3 mm, 0.5-2 mm and numerical values within those ranges) or less than or equal to about 2 mm. The width of each rib 1217 may be substantially constant along a length of the elongate body 1202. The ribs 1217 may extend continuously from the first end 1204 to the second end 1206. Each rib 1217 may begin within 10 mm (or within 5 mm, or within 2 mm) from the first end 1204 and terminate within 10 mm (or within 5 mm or within 2 mm) from the second end 1206.

The elongate body 1202 may include a core surrounded by an outer layer. The outer layer may conform to the shape of the core. The outer layer extends along at least a partial length or an entire length of the core. The outer layer may cover one or both ends of the core and form an outer surface of the insertion end and/or removal end. In other configurations, one or both ends of the core may be exposed from the outer layer. In tampons 1200 with the outer layer, the longitudinal ribs 1217 may be formed substantially entirely or entirely of the outer layer, although in some configurations, fibers of the internal core may form an internal portion of the longitudinal ribs 1217.

The core can be a fibrous structure made with different quantities of fibers depending on absorbency. The core may have between about 1.0 g and about 2.5 g of fibers. For example, the core may be 1.5 g for a regular absorbency tampon or 2 g for a super absorbency tampon. The fibrous construction of the core may be generally constant or vary along a length of the core. For example, the core may include fewer fibers or less density at the insertion end compared to the removal end.

The outer layer may include a nonwoven material, which may be the same or different from the core material of the elongate body 1202. The nonwoven material may be natural or synthetic, including but not limited to materials such as polyestradiol phosphate, cotton, organic cotton and other organic materials, unbleached cotton and other materials, polypropylene or polyethylene based nonwoven materials, filament nonwoven fabric, synthetic fibers, rayon, viscose, lyocell, bamboo, foam, modified cross-section fiber, trilobal cellulosic fiber, or a blend including any of the aforementioned materials. The outer layer may be sealed at the first end 1204 such that the core is completely covered at the first end 1204. The overwrap layer may be applied to the fibrous core using different methods, for example by embossing a calendered sliver of the fibrous absorbent material with the outer layer, inserting the core into a tube-shaped outer layer, or applying the outer layer as a flat sheet to the core.

Referring back to FIG. 8, in one example, the outer or cover layer may be provided over the elongate body in step 462. The rectangle of the outer layer material may be formed into a tube by sealing two edges of the rectangle together. One end of the tube may be sealed, for example with a heat seal. The elongate body may be inserted into the outer layer tube.

Figure 17A:
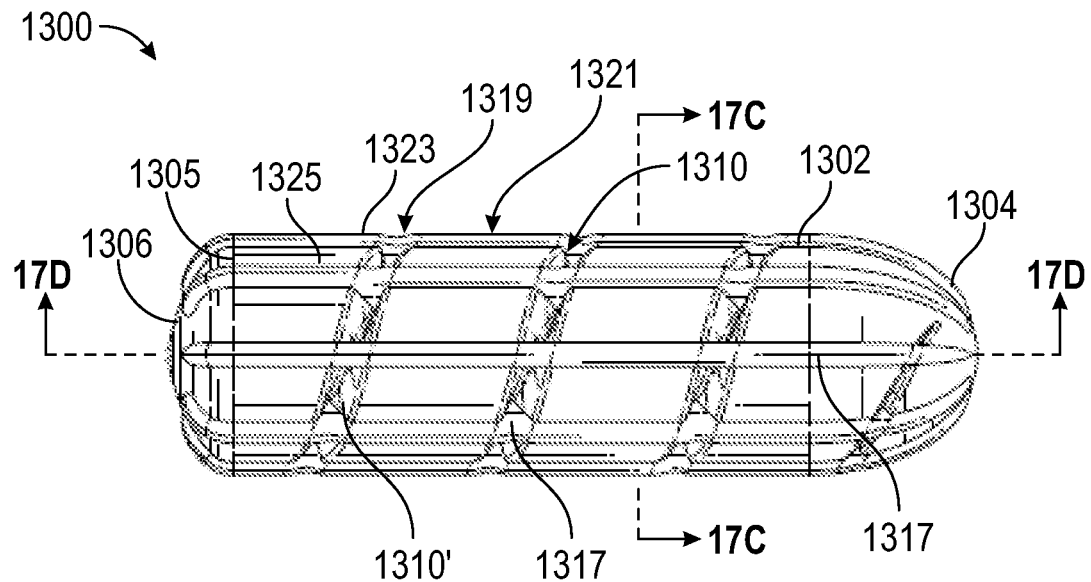
FIGS. 17A and 17B illustrate another tampon having longitudinal ribs.
Figure 17B:
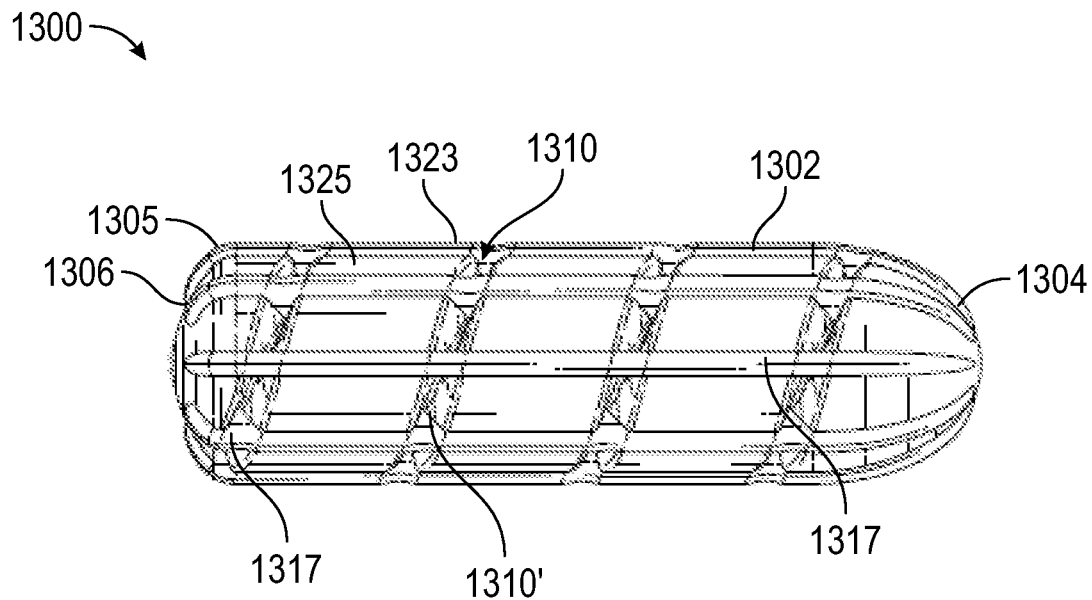

FIGS. 17A and 17B show another tampon 1300 that is similar to the tampon 1200 except as described below. As mentioned above, the longitudinal ribs may converge toward each other at or near the first end of the tampon. In FIGS. 16A and 16B, the longitudinal ribs 1217 converge at the first end 1204 to form the insertion tip of the tampon 1200. Alternatively, the ends of the longitudinal ribs 1317 may be spaced apart from the insertion tip of the tampon 1300 as shown in FIGS. 17A and 17B. The first end 1304 of the tampon 1300 may include a rounded surface to facilitate insertion. The first end 1304 may be covered by the outer layer.

After forming the elongate body using any of the methods described above, the flow path may be molded into the outer surface of the elongate body, for example using a radial compression mold. The localized compression along the flow path extends the length of the flow path and adds more surface area. Because there is a longer path and more contact with the fibers, the rate of fluid flow is slowed in the longitudinal direction. The slower fluid flow provides more time for the elongate body to absorb fluid, promotes full saturation of the tampon, and delays possible leakage. The fibrous construction of the longitudinal ribs may be less dense than the compressed fibers along the flow path.

Figure 17C:
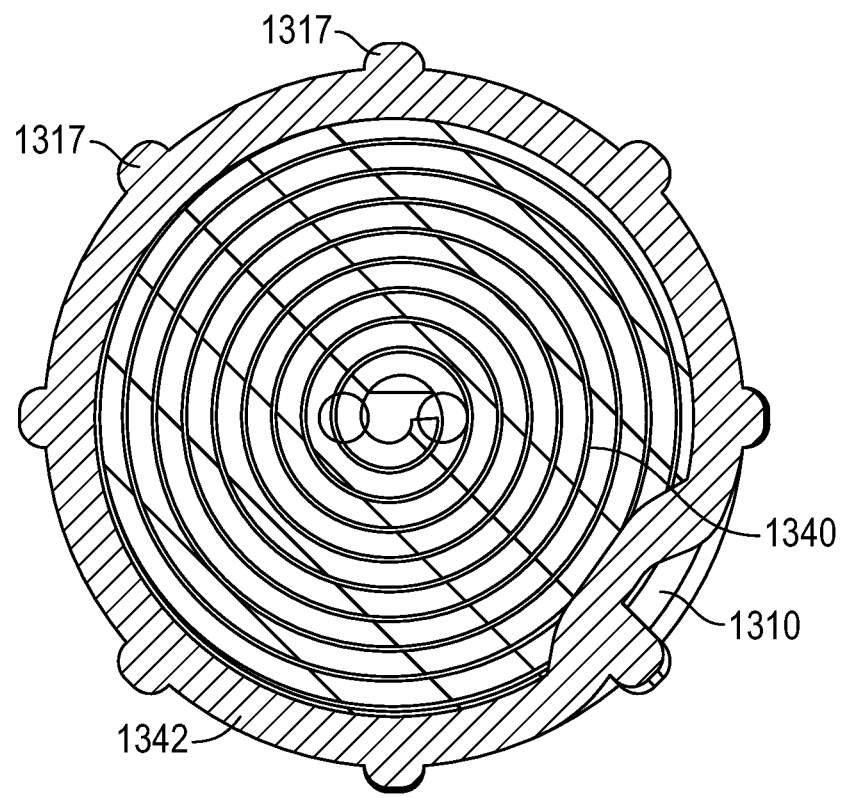
FIGS. 17C and 17D illustrate cross-sections of the tampon shown in FIG. 17A.
Figure 17D:
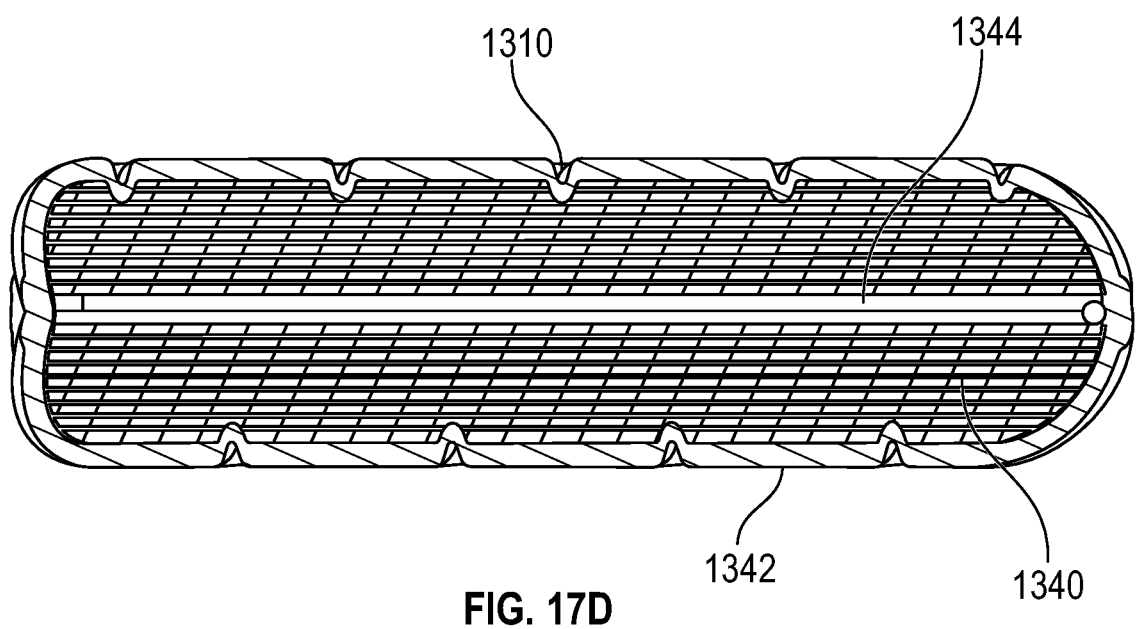

FIG. 17C illustrates a transverse cross-section of the tampon 1300. As illustrated, the core 1340 is rolled up, for example in a swiss roll design, to form the elongate body 1302. The longitudinal ribs 1317 are formed substantially from the outer layer 1342. As shown in FIG. 17D, the withdrawal string 1344 extends through substantially the entire elongate body 1302.

Figure 18A:
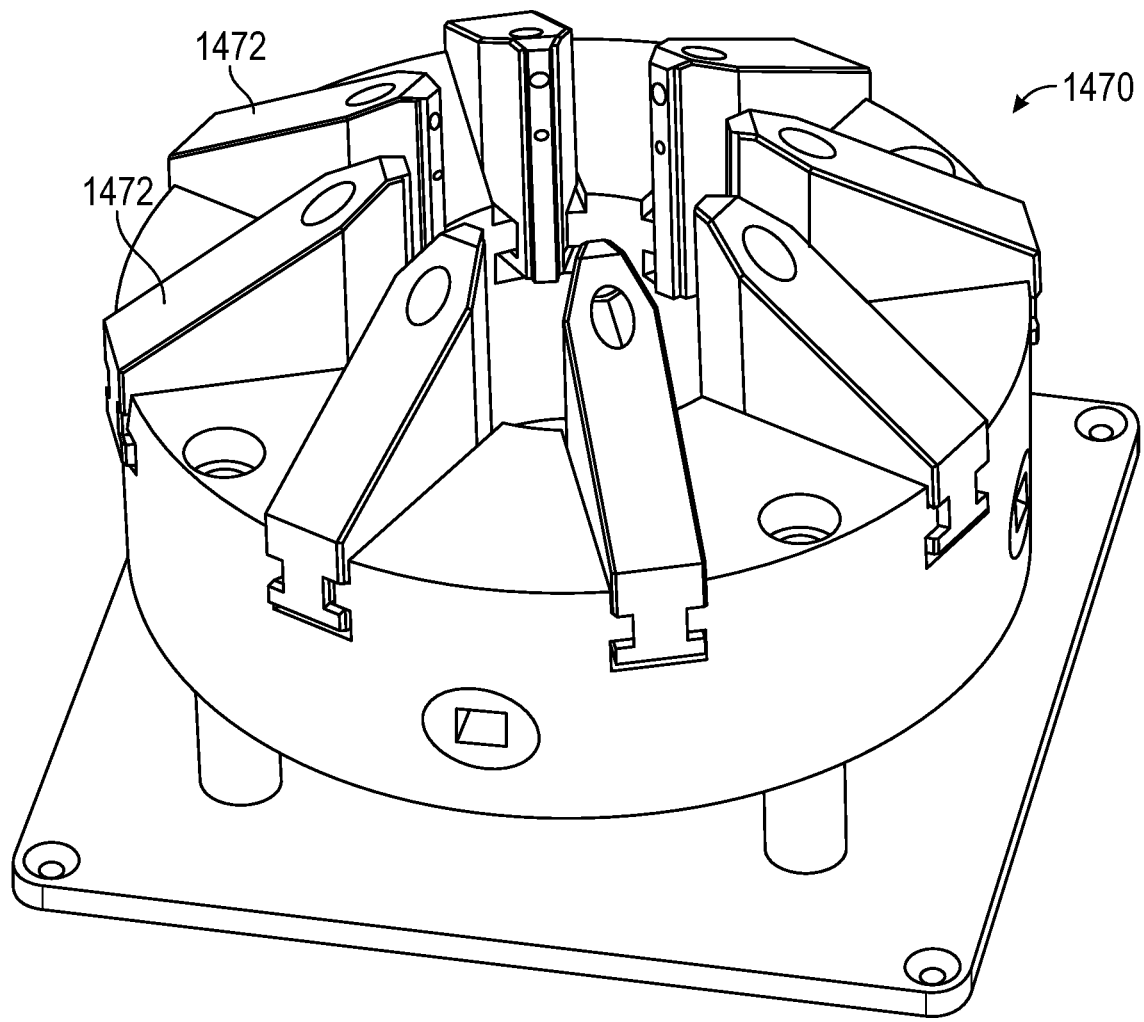
FIGS. 18A and 18B illustrate a mold that may be used to manufacture the tampon shown in FIGS. 16A and 16B.
Figure 18B:
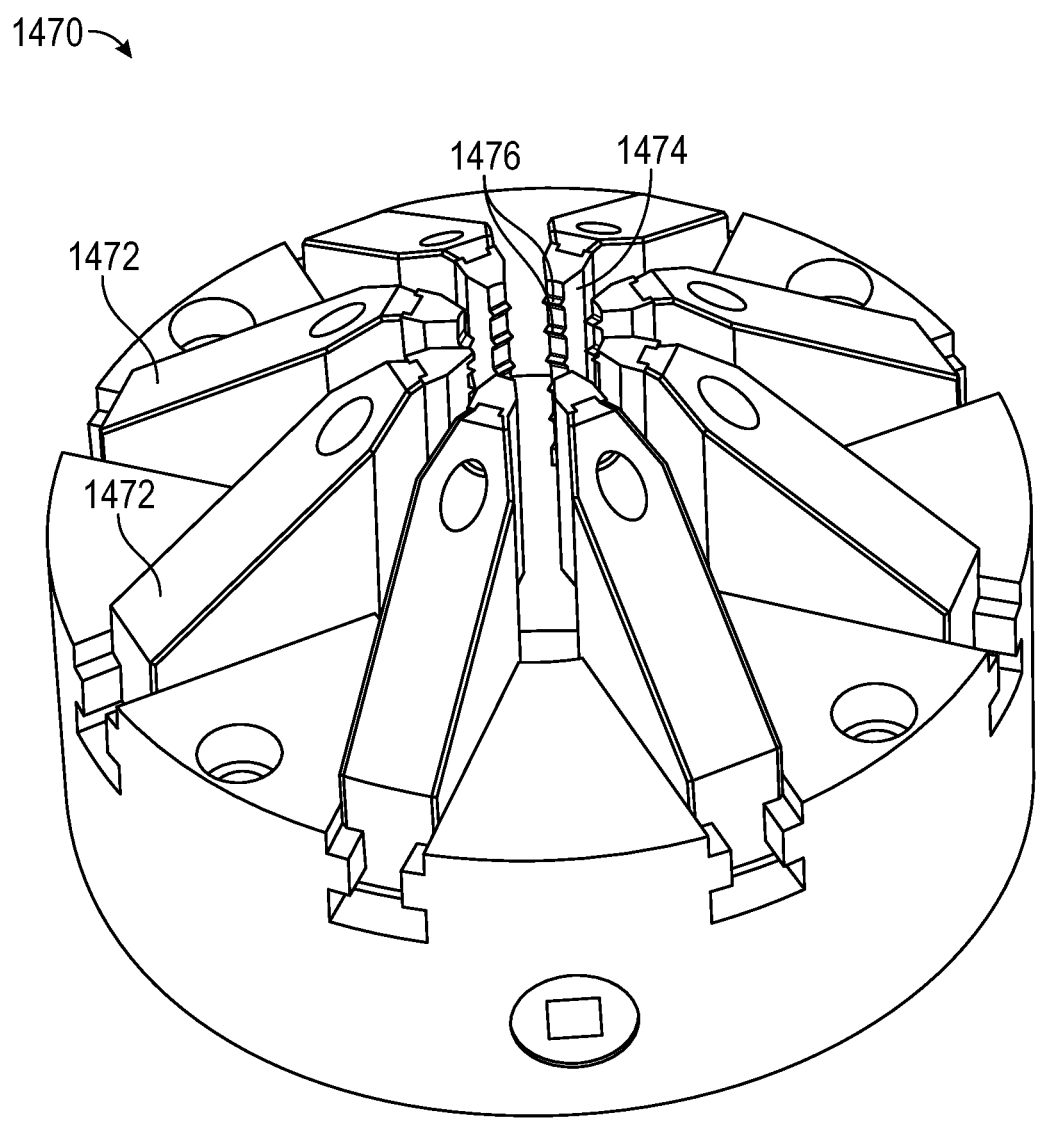

FIGS. 18A and 18B provide an example of a compression mold 1470 to create the tampon 1200, although a similar mold could be used to create the tampon 1300. The compression mold 1470 includes one or more mold segments 1472 disposed circumferentially around the mold 1470. Each mold segment 1472 may be tapered toward a center of the mold 1470. Each segment 1472 may span between 30 degrees and 180 degrees of the elongate body, for example between 45 degrees and 90 degrees of the elongate body. In use, the formed tampon may be disposed at the center of the one or more mold segments 1472. As the one or more mold segments 1472 move radially inward toward the elongate body, e.g., from FIG. 18A to FIG. 18B, the flow path is formed in the outer surface of the elongate body. This compression process may be manual or automated.

As illustrated in FIG. 18B, each mold segment 1472 may include a body portion 1474 and one or more projections 1476 projecting from the body portion 1374. The body portion 1474 may be constructed of aluminum. Each projection 1476 may form a negative of a flow segment of the flow path to be created on the elongate body. Together, the projections form the generally spiral flow path. When the mold segments 1472 are compressed inward, space remains between adjacent mold segments 1472. The longitudinal ribs are extruded through the space between adjacent mold segments 1472. The upper ends of the body portions 1474 converge toward each other to cinch the insertion end of the tampon.

Although a particular manufacturing method is described with respect to FIGS. 18A and 18B, the tampons described herein may be manufactured using other methods. For example, after the elongate body is formed, the elongate body may be twisted to form the flow path prior to forming the longitudinal ribs.

In several embodiments, a single tampon may include a combination of any of the flow paths and ribs described above. In any of the above-described tampons, the tampon may have the described flow path or ribs to the exclusion of any other flow paths, particularly without any longitudinal grooving, substantially longitudinal grooving, or grooving that makes less than a full turn around a circumference of the elongate body. For example, the tampon may have a single, continuous flow path to the exclusion of any other flow paths. The single, continuous flow path may have a single starting point at or near the insertion end of the elongate body and a single termination point at or near the removal end of the elongate body. In any of the above-mentioned external flow paths, the flow path may terminate at the removal end of the elongate body without extending across the end face of the removal end (e.g., the flattened base). As another example, the tampon may include the longitudinal ribs without the spiral flow path or any other flow paths.

In several embodiments, the above-described tampons improve the efficiency of absorbency compared to similar sized tampons on the market. As a result, the total time that elapses prior to leakage is longer compared to similar sized tampons on the market. For women with a heavier menstrual flow, the tampon designs described herein may allow a user to use a smaller sized tampon or tampon having a lower absorbency rating because the tampon is more likely to reach full saturation before leaking. The smaller sized tampon may be less noticeable to the user and reduce discomfort during removal.

As described above, the annular or spiral flow paths described herein lengthen the total flow path for menstrual material. For women with more viscous menses or blood clots, the flow path provides greater travel for the viscous menstrual material and gives the tampon additional time to absorb the menstrual material. A total length of the flow path can be at least about 100 mm, for example between about 150 mm and about 250 mm or between about 175 mm and about 225 mm. The total length of the flow path can be at least two or three times greater than a length of the elongate body, for example between about three and about five. This reduces the likelihood of possible leakage before full saturation of tampon, so women do not have to continually worry about checking their tampons.

Since the tampons described herein are capable of absorbing a greater amount of fluid before leaking, less frequent replacement of tampons is needed. This lowers the total number of products needed during a menstrual cycle. In several embodiments, the tampons include external flow paths that conform to the rugae along the vaginal walls to prevent displacement of the tampon during active movement. Any of the above-mentioned tampons may also include a sustainable material, such as bamboo that provides higher absorbency and antibacterial properties.

Any of the tampons described herein can be inserted using an applicator or digitally inserted. As the tampon is inserted, the tampon may generally expand in an axial and/or radial direction. For tampons inserted using the applicator, the applicator may be made of a plastic or cardboard material. The applicator may include an outer tubular body and an inner plunger. The outer tubular body may have a smooth surface and/or a rounded end to facilitate insertion. An insertion end of the outer tubular body has an opening for deployment of the tampon. The inner plunger may be slidably disposed within the outer tubular body to facilitate ejection of the tampon. The inner plunger may take the form of an inner tubular body.

Any of the above-described tampons may be provided in a kit. For example, the kit may include a plurality of any of the above-mentioned tampons or a combination of any of the above-mentioned tampons. For any given type of tampon within the kit, there may be tampons having a different absorbency rating. For example, the kit may include one or more tampons of the same type (e.g., absorbent material and/or flow path design) having a light absorbency, regular absorbency, super absorbency, super plus absorbency, and/or ultra-absorbency rating to allow the user to accommodate different levels of flow during a menstrual cycle. Within any given type of tampon, the absorbency may be adjusted based on a mass of the tampon and/or the dimensions of the flow path. The change in absorbency only impacts the weight, circumference, and/or size of the tampon, not the structure or proportions of the design. The plurality of tampons may be sufficient to last a user for one menstrual cycle or multiple menstrual cycles, for example three menstrual cycles. The kit may include at least two to eight tampons per day of the menstrual cycle. The kit may additionally include one or more liners, pads, and/or period underwear.

The tampons described herein may have one or more regions of fluid impervious or fluid wicking regions. In some embodiments, the tampon comprises at least one region that is less or more absorbent than other regions. In some embodiments, the core of the tampon is comprised of filler material or other material that is different (in material and/or absorbency) than the rest of the tampon. Although certain tampons have been described herein in connection with menstrual cycle, the tampons described herein can be used for wound healing, nose bleeds, surgical sites, fecal incontinence, or absorption of any other bodily fluids. In some embodiments, the tampon can be a plug or other body for absorbing bodily fluid. The tampon may take on a shape other than the elongate shape illustrated herein. For example, the tampon may have a conical, bulbous, flattened, or other shaped body. The tampon may be used to deliver medications to the body. The medicated portion may be a separate portion on and/or in the tampon, or the tampon may be coated or embedded with the medication. The medication may be helpful for analgesia, dysmenorrhea, blood flow and clotting, antimicrobial activity, etc. In some embodiments, the tampon is designed to expand (e.g., self-expand, expand upon release of constraint, expand upon exposure to body temperature, expand upon fluid exposure, etc.)

The ranges disclosed herein also encompass any and all overlap, sub-ranges, and combinations thereof. Language such as "up to," "at least," "greater than," "less than," "between," and the like includes the number recited. Numbers preceded by a term such as "about," "approximately," or "near" include the recited numbers and should be interpreted based on the circumstances (e.g., as accurate as reasonably possible under the circumstances, for example ±1%, ±5%, ±10%, ±15%, etc.). For example, "about 2 mm" includes "2 mm." Phrases preceded by a term such as "substantially" or "generally" include the recited phrase and should be interpreted based on the circumstances (e.g., as much as reasonably possible under the circumstances). For example, "generally longitudinal" includes "longitudinal."

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

Although certain embodiments and examples have been described herein, it will be understood by those skilled in the art that many aspects of the tampons shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:

1. A tampon comprising:

an elongate body comprising an insertion end and a removal end opposite the insertion end, a longitudinal axis of the elongate body extending through the removal end and the insertion end;

a plurality of longitudinal ribs protruding from an outer surface of the elongate body;

a flow path recessed in an outer surface of the elongate body, the flow path turning about the longitudinal axis of the body, the flow path being angled closer to horizontal than the longitudinal axis of the body; and a removal string extending from the removal end of the elongate body.

2. The tampon of claim 1, wherein the flow path is configured to direct a flow of menses in a spiral path around the elongate body.

3. The tampon of claim 1, wherein the flow path comprises a plurality of recessed segments disposed between adjacent longitudinal ribs.

4. The tampon of claim 1, wherein the flow path comprises a spiral recess, each of the plurality of longitudinal ribs crossing successive turns of the spiral recess.

5. The tampon of claim 4, wherein the plurality of longitudinal ribs extend into the flow path where the plurality of longitudinal ribs cross the flow path.

6. The tampon of claim 1, wherein the plurality of longitudinal ribs converge toward the insertion end to form a tip of the tampon.

7. The tampon of claim 1, wherein the plurality of longitudinal ribs are spaced apart from the insertion end of the elongate body.

8. The tampon of claim 1, wherein the flow path is angled between 50 degrees and 80 degrees from the longitudinal axis of the elongate body.

9. The tampon of claim 1, wherein each of the plurality of longitudinal ribs extends across at least a majority of a length of the elongate body.

10. The tampon of claim 1, wherein each of the plurality of longitudinal ribs comprises an outer edge, the outer edge being recessed at a first location crossing the flow path compared to a second location away from the flow path.

11. A tampon comprising:

an elongate body comprising an insertion end and a removal end opposite the insertion end, a longitudinal axis of the elongate body extending through the removal end and the insertion end;

a plurality of ribs protruding from an outer surface of the elongate body; and a spiral flow path recessed in an outer surface of the elongate body, the spiral flow path turning about the longitudinal axis of the body; and a removal string extending from the removal end of the elongate body.

12. The tampon of claim 11, wherein the elongate body comprises an absorbent core surrounded by an overwrap layer.

13. The tampon of claim 12, wherein the overwrap layer is sealed at the insertion end.

14. The tampon of claim 13, wherein the absorbent core is exposed at the removal end.

15. The tampon of claim 12, wherein the plurality of ribs are formed only by the overwrap layer.

16. A tampon comprising:

an elongate body comprising an insertion end and a removal end opposite the insertion end, a longitudinal axis of the elongate body extending through the removal end and the insertion end;

a plurality of flow path segments recessed in an outer surface of the elongate body, each flow path segment being angled closer to horizontal than the longitudinal axis of the elongate body; and a plurality of longitudinal ribs protruding from an outer surface of the elongate body, the plurality of longitudinal ribs separating the plurality of flow path segments.

17. The tampon of claim 16, wherein the elongate body comprises an absorbent core surrounded by an overwrap layer.

18. The tampon of claim 17, wherein the overwrap layer is sealed at the insertion end.

19. The tampon of claim 18, wherein the absorbent core is exposed at the removal end.

20. The tampon of claim 17, wherein the plurality of longitudinal ribs are formed only by the overwrap layer.

21. The tampon of claim 16, wherein the plurality of flow path segments combine to form a spiral flow path.

* * * * *